US012648693B2

(12) United States Patent
Nakazawa et al.

(10) Patent No.: US 12,648,693 B2
(45) Date of Patent: Jun. 9, 2026

(54) OPHTHALMIC INFORMATION PROCESSING APPARATUS, OPHTHALMIC APPARATUS, OPHTHALMIC INFORMATION PROCESSING METHOD, AND RECORDING MEDIUM

(71) Applicants: Topcon Corporation, Tokyo (JP); TOHOKU UNIVERSITY, Sendai (JP); RIKEN, Saitama (JP)

(72) Inventors: Toru Nakazawa, Sendai (JP); Kazuko Omodaka, Sendai (JP); Hideo Yokota, Wako (JP); Guangzhou An, Tokyo (JP); Tsutomu Kikawa, Tokyo (JP)

(73) Assignees: TOPCON CORPORATION, Tokyo (JP); TOHOKU UNIVERSITY, Seddai (JP); RIKEN, Wako (JP)

( * ) Notice: Subject to any disclaimer, the term of this patent is extended or adjusted under 35 U.S.C. 154(b) by 466 days.

(21) Appl. No.: 18/142,043

(22) Filed: May 2, 2023

(65) Prior Publication Data
US 2023/0263391 A1     Aug. 24, 2023

Related U.S. Application Data

(63) Continuation of application No. PCT/JP2021/040330, filed on Nov. 2, 2021.

(30) Foreign Application Priority Data
Nov. 4, 2020     (JP) ................................. 2020-184091

(51) Int. Cl.
*A61B 3/12*     (2006.01)
*A61B 3/14*     (2006.01)
*G06T 7/00*     (2017.01)

(52) U.S. Cl.
CPC .................. *A61B 3/12* (2013.01); *A61B 3/14* (2013.01); *G06T 7/0012* (2013.01); *G06T 2207/20081* (2013.01); *G06T 2207/30041* (2013.01)

(58) Field of Classification Search
CPC ........... A61B 3/12; A61B 3/14; G06T 7/0012; G06T 2207/20081; G06T 2207/30041;
(Continued)

(56) References Cited

U.S. PATENT DOCUMENTS

2012/0157820 A1* 6/2012 Zhang ................... G06T 7/0014
                                                                600/407
2016/0317013 A1* 11/2016 Ogata .................. A61B 3/0008
(Continued)

FOREIGN PATENT DOCUMENTS

CN         111179258 A     5/2020
CN         111383775 A     7/2020
(Continued)

OTHER PUBLICATIONS

Japanese Office Action issued Oct. 1, 2024, in corresponding Japanese Patent Application No. 2020-184091, 6pp.
International Search Report and Written Opinion mailed on Dec. 21, 2021, received for PCT Application PCT/JP2021/040330, filed on Nov. 2, 2021, 10 pages including English Translation.
Jha et al., "ResUNet++: An Advanced Architecture for Medical Image Segmentation", arXiv:1911.07067v1 [eess.IV], Nov. 16, 2019, 7 pages.
(Continued)

*Primary Examiner* — Mohammed A Hasan
(74) *Attorney, Agent, or Firm* — XSENSUS LLP

(57) ABSTRACT
An ophthalmic information processing apparatus includes a determiner and a detector. The determiner is configured to determine a presence or absence of a disc hemorrhage for a front image of a fundus of a subject's eye, using a disc hemorrhage determination model obtained by performing machine learning using a plurality of fundus images labeled with labels indicating the presence or absence of a disc hemorrhage as first teaching data. The detector is configured to detect a disc hemorrhage region depicted in the front
(Continued)

image that is determined to have the disc hemorrhage, using a disc hemorrhage region detection model obtained by performing machine learning using a plurality of pairs of image groups as second teaching data, each pair having a front image of a fundus and a disc hemorrhage region image representing a disc hemorrhage region depicted in the front image.

25 Claims, 16 Drawing Sheets

(58) Field of Classification Search
CPC . G06T 2207/10024; G06T 2207/10101; G06T 2207/20084
USPC ......................................................... 351/206
See application file for complete search history.

(56) References Cited

U.S. PATENT DOCUMENTS

| | | | |
|---|---|---|---|
| 2018/0153401 A1* | 6/2018 | Strózyk | A61B 3/117 |
| 2018/0303334 A1* | 10/2018 | Tokuyama | A61B 3/0041 |
| 2019/0082957 A1* | 3/2019 | Fujii | A61B 3/102 |
| 2021/0150713 A1 | 5/2021 | Takei | |

FOREIGN PATENT DOCUMENTS

| | | |
|---|---|---|
| JP | 2008-073280 A | 4/2008 |
| JP | 2013-022028 A | 2/2013 |
| WO | 2020/054188 A1 | 3/2020 |

OTHER PUBLICATIONS

Office Action issued Jul. 9, 2024 in Japanese Patent Application No. 2020-184091 with English translation thereof.

* cited by examiner

FIG. 6

OPHTHALMIC INFORMATION PROCESSING APPARATUS, OPHTHALMIC APPARATUS, OPHTHALMIC INFORMATION PROCESSING METHOD, AND RECORDING MEDIUM

CROSS-REFERENCE TO RELATED APPLICATIONS

The present application is a continuation application of International Patent Application No. PCT/JP2021/040330, filed Nov. 2, 2021, which claims priority to Japanese Patent Application No. 2020-184091, filed Nov. 4, 2020, both of which are herein incorporated by reference in their entirety.

FIELD

The disclosure relates to an ophthalmic information processing apparatus, an ophthalmic apparatus, an ophthalmic information processing method, and a recording medium.

BACKGROUND

Glaucoma is a disease ranking high in causes of blindness. Optic nerve neuropathy and visual field deficit caused by glaucoma are essentially progressive and irreversible, progressing gradually without patient awareness. Therefore, arrestation or inhibition of progression of the disorder by early detection and early treatment of glaucoma is very important.

One of these risk factors for the progression of glaucoma is disc hemorrhage. For example, the doctors determine the presence or absence of the disc hemorrhage by observing a fundus image acquired using a fundus camera. Such doctors are required to use their enough experience and knowledge to determine the presence or absence of the disc hemorrhage with a high degree of accuracy.

For example, Japanese Unexamined Patent Application Publication No. 2008-73280 discloses a method of extracting a fundus hemorrhage, hemorrhagic area, and an optic disc region, using pixel value differences in a color fundus image.

SUMMARY

One aspect of embodiments is an ophthalmic information processing apparatus, including: a determiner configured to determine a presence or absence of a disc hemorrhage for a front image of a fundus of a subject's eye, using a disc hemorrhage determination model obtained by performing machine learning using a plurality of fundus images labeled with labels indicating the presence or absence of a disc hemorrhage as first teaching data; and a detector configured to detect a disc hemorrhage region depicted in the front image that is determined to have the disc hemorrhage by the determiner, using a disc hemorrhage region detection model obtained by performing machine learning using a plurality of pairs of image groups as second teaching data, each pair having a front image of a fundus and a disc hemorrhage region image representing a disc hemorrhage region depicted in the front image.

Another aspect of the embodiments is an ophthalmic apparatus, including: an imaging unit configured to image the fundus of the subject's eye; and the ophthalmic information processing apparatus described above.

Still another aspect of the embodiments is an ophthalmic apparatus, including: an imaging unit configured to image the fundus of the subject's eye; an OCT unit configured to acquire the OCT data by performing optical coherence tomography on the subject's eye; and the ophthalmic information processing apparatus described above.

Still another aspect of the embodiments is an ophthalmic information processing method, including: a determination step of determining a presence or absence of a disc hemorrhage for a front image of a fundus of a subject's eye, using a disc hemorrhage determination model obtained by performing machine learning using a plurality of fundus images labeled with labels indicating the presence or absence of a disc hemorrhage as first teaching data; and a detection step of detecting a disc hemorrhage region depicted in the front image that is determined to have the disc hemorrhage in the determination step, using a disc hemorrhage region detection model obtained by performing machine learning using a plurality of pairs of image groups as second teaching data, each pair having a front image of a fundus and a disc hemorrhage region image representing a disc hemorrhage region depicted in the front image.

Still another aspect of the embodiments is a computer readable non-transitory recording medium in which a program for causing a computer to execute each step of the ophthalmic information processing method of described above is recorded.

BRIEF DESCRIPTION OF THE DRAWINGS

FIG. 6 is a schematic diagram illustrating an example of the configuration of the ophthalmic apparatus according to the first embodiment.

DETAILED DESCRIPTION

Figure 1:
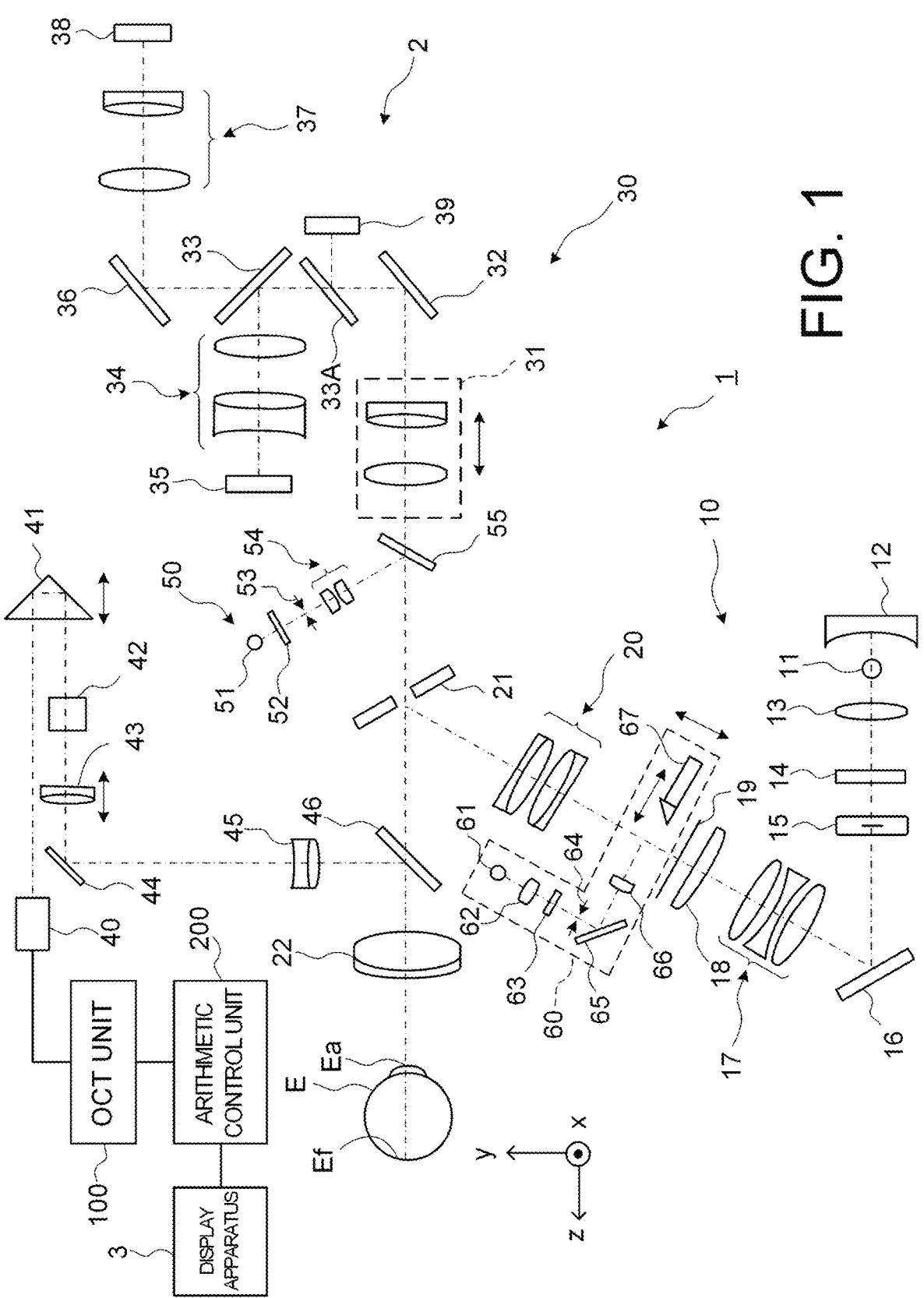
FIG. 1 is a schematic diagram illustrating an example of a configuration of an ophthalmic apparatus according to a first embodiment.

In fundus images, the overall hue and pixel values in the sites and blood vessels vary depending on the subject's eye. Therefore, it is considered that it is often difficult to extract hemorrhagic areas, etc. with high accuracy using only pixel value differences as in conventional methods. Besides, it would be even more difficult to precisely identify the position of the hemorrhage area, such as whether the position of the hemorrhage area is within the optic disc region or not. Unless the hemorrhagic areas can be detected with a high degree of accuracy, the doctors cannot determine with high reproducibility and precision whether or not the disc hemorrhage is present.

According to some embodiments of the present invention, a new technique for detecting disc hemorrhage with high reproducibility and high accuracy can be provided.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Referring now to the drawings, exemplary embodiments of an ophthalmic information processing apparatus, an ophthalmic apparatus, an ophthalmic information processing method, and a recording medium according to the present invention are described below. Any of the contents of the documents cited in the present specification and arbitrary known techniques may be applied to the embodiments below.

An ophthalmic information processing apparatus according to embodiments is configured to determine the presence or absence of a disc hemorrhage for a fundus image of a subject's eye using a learned model, and to detect a disc hemorrhage region depicted in the fundus image that is determined to have the disc hemorrhage using another learned model. The learned model used to determine the presence or absence of the disc hemorrhage is a disc hemorrhage determination model obtained by performing machine learning using a plurality of fundus images labeled with labels indicating the presence or absence of the disc hemorrhage as first teaching data. The learned model used to detect the disc hemorrhage region is a disc hemorrhage region detection model obtained by performing machine learning using a plurality of pairs of image groups as second teaching data, each pair having a front image of a fundus and a disc hemorrhage region image representing a disc hemorrhage region depicted in the front image. The fundus image is preferably a color front image of the fundus obtained by photographing the fundus with a fundus camera, etc.

This allows to update learning parameters of the disc hemorrhage region detection model specifically for detection of the disc hemorrhage region, by generating the disc hemorrhage region detection model by performing machine learning using the fundus images alone in which the disc hemorrhage region exists. As a result, the accuracy of detection of the disc hemorrhage region can be improved. Therefore, the disc hemorrhage regions in the fundus images can be detected with higher reproducibility and accuracy, compared to detecting the disc hemorrhage region in the fundus image of the subject's eye using a single learned model.

In some embodiments, the ophthalmic information processing apparatus is configured to analyze the fundus images to generate an analysis result of the disc hemorrhage region detected with high reproducibility and accuracy. The analysis result includes at least one of position information representing a position of the disc hemorrhage region, shape information representing a shape of the disc hemorrhage region, and/or occurrence information representing an occurrence status of the disc hemorrhage region.

In some embodiments, the ophthalmic information processing apparatus is configured to perform position matching between the fundus image that the disc hemorrhage region is detected and OCT (Optical Coherence Tomography) data of the subject's eye. Thereby, the position information and the shape information are generated using the position information of an OCT coordinate system defining the OCT data. This allows to obtain the position information and the shape information of the disc hemorrhage region with high accuracy from the fundus image mapped to the OCT coordinate system that defines highly reproducible OCT data.

In some embodiments, an ophthalmic apparatus has a function of the ophthalmic information processing apparatus according to the embodiments. Here, the ophthalmic apparatus has a function of a fundus camera for acquiring fundus images of the subject's eye and a function of an OCT apparatus (optical coherence tomography) that can perform OCT measurement for acquiring OCT data of the subject's eye.

In some embodiments, the ophthalmic apparatus having the function of the fundus camera has the function of the ophthalmic information processing apparatus according to the embodiments. In this case, the ophthalmic apparatus is configured to acquire the OCT data from an OCT apparatus provided outside the ophthalmic apparatus.

In some embodiments, the ophthalmic apparatus having the function of the OCT apparatus has the function of the ophthalmic information processing apparatus according to the embodiments. In this case, the ophthalmic apparatus is configured to acquire the fundus images from a fundus camera provided outside the ophthalmic apparatus.

In some embodiments, the ophthalmic information processing apparatus is configured to acquire the fundus images from the fundus camera provided outside the ophthalmic information processing apparatus and to acquire the OCT data from the OCT apparatus provided outside the ophthalmic information processing apparatus.

In some embodiments, the ophthalmic information processing apparatus is configured to acquire the fundus images and the OCT data from the ophthalmic apparatus having the function of the fundus camera and the function of the OCT apparatus.

In some embodiments, the fundus image is a C-scan image, a projection image, or an enface image that is formed from the OCT data, or an image that is acquired by an ophthalmic apparatus, such as a scanning laser ophthalmoscope (SLO), a slit lamp ophthalmoscope, or a surgical microscope. In the case that the fundus image is the C-scan image, the projection image, or the en-face image, the position matching between fundus image and the OCT data is not required.

An ophthalmic information processing method according to the embodiments includes one or more steps for realizing the processing executed by a processor (computer) in the ophthalmic information processing apparatus according to the embodiments. A program according to the embodiments causes the processor to execute each step of the ophthalmic information processing method according to the embodiments. A recording medium according to the embodiments is a computer readable non-transitory recording medium (storage medium) on which the program according to the embodiments is recorded.

The term "processor" as used herein refers to a circuit such as, for example, a central processing unit (CPU), a graphics processing unit (GPU), an application specific integrated circuit (ASIC), and a programmable logic device (PLD). Examples of PLD include a simple programmable logic device (SPLD), a complex programmable logic device (CPLD), and a field programmable gate array (FPGA). The processor realizes, for example, the function according to the embodiments by reading out a computer program stored in a storage circuit or a storage device and executing the computer program.

In this specification, an image acquired using OCT may be collectively referred to as an "OCT image". Also, the measurement operation for forming OCT images may be referred to as OCT measurement. Further, the disc hemorrhage may be referred to simply as DH (Disc Hemorrhage).

First Embodiment

An ophthalmic apparatus according to a first embodiment has a function of the fundus camera, a function of the OCT apparatus, and a function of the ophthalmic information processing apparatus according to the embodiments. Further, the ophthalmic apparatus may have function of at least one of an ophthalmic measurement apparatus and an ophthalmic treatment apparatus. In some embodiments, the ophthalmic measuring apparatus includes at least one of an eye refractivity examination apparatus, a tonometer, a specular microscope, a wave-front analyzer, a perimeter, and a microperimeter. In some embodiments, the ophthalmic treatment apparatus includes at least one of a laser treatment apparatus, a surgical apparatus, and a surgical microscope.
<Configuration>
[Optical System]

FIG. 1 shows an example of a configuration of the ophthalmic apparatus according to the first embodiment.

The ophthalmic apparatus 1 according to the first embodiment includes a fundus camera unit 2, an OCT unit 100, and an arithmetic control unit 200. The fundus camera unit 2 is provided with an optical system and a mechanism for acquiring front images of a subject's eye E. The OCT unit 100 is provided with a part of an optical system and a mechanism for performing OCT. Another part of the optical system and the mechanism for performing OCT are provided in the fundus camera unit 2. The arithmetic control unit 200 includes one or more processors for performing various kinds of arithmetic processing and control processing. In addition to these elements, an arbitrary element or a unit, such as a member (chin rest, forehead pad, etc.) for supporting a face of the subject, a lens unit (for example, an attachment for an anterior segment or OCT) for switching the target site of OCT, the like, may be provided in the ophthalmic apparatus 1. In some embodiments, the lens unit is configured to be manually inserted and removed between the subject's eye E and an objective lens 22 described below. In some embodiments, the lens unit is configured to be automatically inserted and removed between the subject's eye E and the objective lens 22 described below, under the control of the controller 210 described below.
[Fundus Camera Unit]

The fundus camera unit 2 is provided with an optical system for imaging (photographing) a fundus Ef of the subject's eye E. An image (called fundus image, fundus photograph, etc.) of the fundus Ef to be obtained is a front image such as an observation image, a captured image. The observation image is obtained by moving image shooting using near infrared light. The captured image is a still image (for example, a color image) using flash light. Furthermore, the fundus camera unit 2 can acquire the front image (anterior segment image) by photographing (imaging) an anterior segment Ea of the subject's eye E.

The fundus camera unit 2 includes an illumination optical system 10 and an imaging (photographing) optical system 30. The illumination optical system 10 irradiates illumination light onto the subject's eye E. The imaging optical system 30 detects returning light of the illumination light from the subject's eye E. Measurement light from the OCT unit 100 is guided to the subject's eye E through an optical path in the fundus camera unit 2. Returning light of the measurement light is guided to the OCT unit 100 through the same optical path.

Light (observation illumination light) emitted from the observation light source 11 of the illumination optical system 10 is reflected by a reflective mirror 12 having a curved reflective surface, and becomes near-infrared light after being transmitted through a visible cut filter 14 via a condenser lens 13. Further, the observation illumination light is once converged near an imaging light source 15, is reflected by a mirror 16, and passes through relay lenses 17 and 18, a diaphragm 19, and a relay lens 20. Then, the observation illumination light is reflected on the peripheral part (the surrounding area of a hole part) of a perforated mirror 21, is transmitted through a dichroic mirror 46, and is refracted by the objective lens 22, thereby illuminating the subject's eye E (fundus Ef or anterior segment Ea). Returning light of the observation illumination light reflected from the subject's eye E is refracted by the objective lens 22, is transmitted through the dichroic mirror 46, passes through the hole part formed in the center region of the perforated mirror 21, is transmitted through a dichroic mirror 55. The returning light transmitted through the dichroic mirror 55 travels through a photography focusing lens 31 and is reflected by a mirror 32. Further, this returning light is transmitted through a half mirror 33A, is reflected by a dichroic mirror 33, and forms an image on the light receiving surface of an image sensor 35 by a condenser lens 34. The image sensor 35 detects the returning light at a predetermined frame rate. It should be noted that the focus of the imaging optical system 30 is adjusted so as to coincide with the fundus Ef or the anterior segment Ea.

Light (imaging illumination light) emitted from the imaging light source 15 is irradiated onto the fundus Ef through the same route as that of the observation illumination light. Returning light of the imaging illumination light from the subject's eye E is guided to the dichroic mirror 33 through the same route as that of the observation illumination light, is transmitted through the dichroic mirror 33, is reflected by a mirror 36, and forms an image on the light receiving surface of the image sensor 38 by a condenser lens 37.

A liquid crystal display (LCD) 39 displays a fixation target and a visual target used for visual acuity measurement. Part of light flux output from the LCD 39 is reflected by the half mirror 33A, is reflected by the mirror 32, travels through the photography focusing lens 31 and the dichroic mirror 55, and passes through the hole part of the perforated mirror 21. The light flux (beam) having passed through the hole part of the perforated mirror 21 is transmitted through the dichroic mirror 46, and is refracted by the objective lens 22, thereby being projected onto the fundus Ef.

By changing the display position of the fixation target on the screen of the LCD 39, the fixation position of the subject's eye E can be changed. Examples of the fixation position include a fixation position for acquiring an image centered at a macula, a fixation position for acquiring an image centered at an optic disc, a fixation position for acquiring an image centered at a fundus center between the macula and the optic disc, a fixation position for acquiring an image of a site (fundus peripheral part) far away from the macula, and the like. The ophthalmic apparatus 1 according to some embodiments includes GUI (Graphical User Interface) and the like for designating at least one of such fixation positions. The ophthalmic apparatus 1 according to some embodiments includes GUI etc. for manually moving the fixation position (display position of the fixation target).

The configuration for presenting the movable fixation target to the subject's eye E is not limited to the display device such LCD or the like. For example, the movable fixation target can be generated by selectively turning on a plurality of light sources of a light source array (light emitting diode (LED) array or the like). Alternatively, the movable fixation target can be generated using one or more movable light sources.

Further, the ophthalmic apparatus 1 may be provided with one or more external fixation light sources. One of the one or more external fixation light sources can project fixation light onto a fellow eye of the subject's eye E. A projected position of the fixation light on the fellow eye can be changed. By changing the projected position of the fixation light on the fellow eye, the fixation position of the subject's eye E can be changed. The fixation position projected by the external fixation light source(s) may be the same as the fixation position of the subject's eye E using the LCD 39. For example, the movable fixation target can be generated by selectively turning on the plurality of external fixation light sources. Alternatively, the movable fixation target can be generated using one or more movable external fixation light sources.

The alignment optical system 50 generates an alignment indicator for alignment of the optical system with respect to the subject's eye E. Alignment light emitted from an LED 51 travels through the diaphragms 52 and 53 and the relay lens 54, is reflected by the dichroic mirror 55, and passes through the hole part of the perforated mirror 21. The light having passed through the hole part of the perforated mirror 21 is transmitted through the dichroic mirror 46, and is projected onto the subject's eye E by the objective lens 22. Corneal reflection light of the alignment light is guided to the image sensor 35 through the same route as the returning light of the observation illumination light. Manual alignment or automatic alignment can be performed based on the received light image (alignment indicator image) thereof.

The focus optical system 60 generates a split indicator used for adjusting the focus with respect to the subject's eye E. The focus optical system 60 is movable along an optical path (illumination optical path) of the illumination optical system 10 in conjunction with the movement of the photography focusing lens 31 along an optical path (imaging optical path) of the imaging optical system 30. The reflection rod 67 can be inserted and removed into and from the illumination optical path. To perform focus adjustment, the reflective surface of the reflection rod 67 is arranged in a slanted position on the illumination optical path. Focus light emitted from an LED 61 passes through a relay lens 62, is split into two light fluxes by a split indicator plate 63, passes through a two-hole diaphragm 64, is reflected by a mirror 65, and is reflected after an image is once formed on the reflective surface of the reflection rod 67 by a condenser lens 66. Further, the focus light travels through the relay lens 20, is reflected by the perforated mirror 21, is transmitted through the dichroic mirror 46, and is refracted by the objective lens 22, thereby being projected onto the fundus Ef. Fundus reflection light of the focus light is guided to the image sensor 35 through the same route as the corneal reflection light of the alignment light. Manual focus or automatic focus can be performed based on the received light image (split indicator image) thereof.

The dichroic mirror 46 combines an optical path for imaging and an optical path for OCT (optical path of the interference optical system). The dichroic mirror 46 couples an optical axis of the optical path for imaging (imaging optical system 30) and an optical axis of the optical path for OCT (interference optical system) so that the optical axis of the optical path for imaging and the optical axis of the optical path for OCT are approximately coaxial. The dichroic mirror 46 reflects light of wavelength band used in OCT, and transmits light for fundus imaging. The optical path for OCT (optical path of measurement light) is provided with, in order from the OCT unit 100 side to the dichroic mirror 46 side, a collimator lens unit 40, an optical path length changing unit 41, an optical scanner 42, an OCT focusing lens 43, a mirror 44, and a relay lens 45.

The optical path length changing unit 41 is configured to move in direction indicated by the arrow shown in FIG. 1, thereby changing the length of the optical path for OCT. This change in the optical path length is used for correcting the optical path length according to the axial length, adjusting the interference state, or the like. The optical path length changing unit 41 includes a corner cube and a mechanism for moving the corner cube.

The optical scanner 42 is disposed at a position optically conjugate to the pupil of the subject's eye E. The optical scanner 42 deflects the measurement light LS traveling along the OCT optical path. The optical scanner 42 can deflect the measurement light LS in a one-dimensionally or two-dimensional manner.

In case of deflecting the measurement light LS in a one-dimensionally manner, the optical scanner 42 includes a galvano scanner capable of deflecting the measurement light LS within a predetermined deflection angle range in a predetermined deflection direction. In case of deflecting the measurement light LS in a two-dimensionally manner, the optical scanner 42 includes a first galvano scanner and a second galvano scanner. The first galvano scanner deflects the measurement light LS so as to scan an imaging site (fundus Ef or the anterior segment Ea) in a horizontal direction orthogonal to the optical axis of the interference optical system (OCT optical system). The second galvano scanner deflects the measurement light LS deflected by the first galvano scanner so as to scan the imaging site in a vertical direction orthogonal to the optical axis of the interference optical system. Examples of scan mode with the measurement light LS performed by the optical scanner 42 include horizontal scan, vertical scan, cross scan, radial scan, circle scan, concentric scan, helical (spiral) scan, and the like.

The OCT focusing lens 43 is moved along the optical path of the measurement light LS in order to perform focus adjustment of the optical system for OCT. The OCT focusing lens 43 can move within a moving range. The moving range includes a first lens position for placing the focal position of the measurement light LS at the fundus Ef or near the fundus Ef of the subject's eye E and a second lens position for making the measurement light LS projected onto the subject's eye E a parallel light beam. The movement of the photography focusing lens 31, the movement of the focus optical system 60, and the movement of the OCT focusing lens 43 can be controlled in conjunction with each other.

[OCT Unit]

Figure 2:
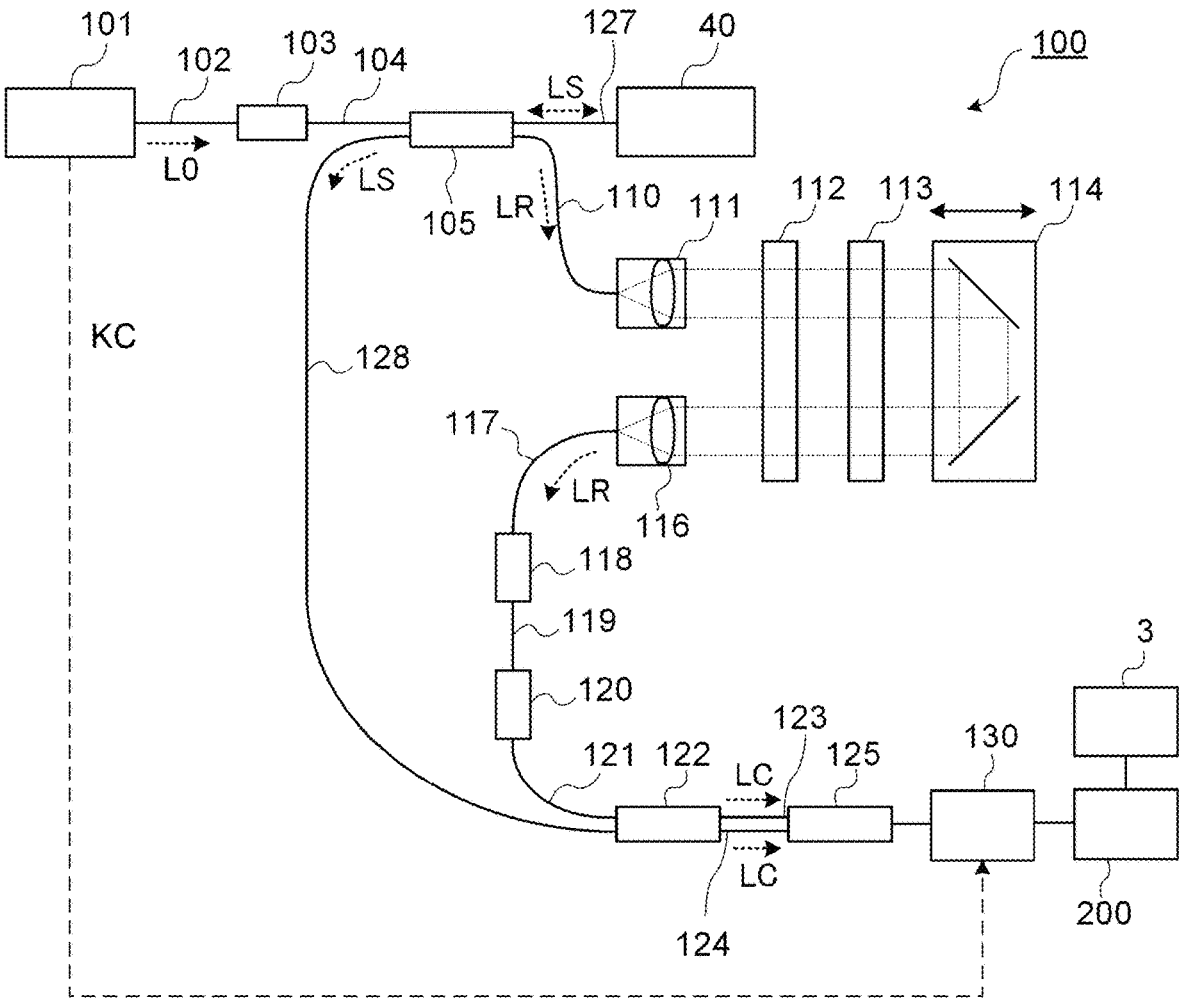
FIG. 2 is a schematic diagram illustrating an example of the configuration of the ophthalmic apparatus according to the first embodiment.

An example of the configuration of the OCT unit 100 is shown in FIG. 2. The OCT unit 100 is provided with an optical system for acquiring OCT images of the subject's eye E. This optical system is an interference optical system that splits light from a wavelength sweeping type (i.e., a wavelength scanning type) light source into measurement light and reference light, makes the measurement light returning from the subject's eye E and the reference light having traveled through the reference optical path interfere with each other to generate interference light, and detects the interference light. The detection result of the interference light obtained by the interference optical system (i.e., the detection signal) is an interference signal indicating the spectrum of the interference light, and is sent to the arithmetic control unit 200.

Like swept source type ophthalmic apparatuses commonly used, the light source unit 101 includes a wavelength sweeping type (i.e., a wavelength scanning type) light source capable of sweeping (scanning) the wavelengths of emitted light. The wavelength sweeping type light source includes a laser light source that includes a resonator. The light source unit 101 temporally changes the output wavelengths within the near-infrared wavelength bands that cannot be visually recognized with human eyes.

Light L0 output from the light source unit 101 is guided to the polarization controller 103 through the optical fiber 102, and the polarization state of the light L0 is adjusted. The polarization controller 103, for example, applies external stress to the looped optical fiber 102 to thereby adjust the polarization state of the light L0 guided through the optical fiber 102.

The light L0 whose the polarization state has been adjusted by the polarization controller 103 is guided to the fiber coupler 105 through the optical fiber 104, and is split into the measurement light LS and the reference light LR.

The reference light LR is guided to the collimator 111 through the optical fiber 110. The reference light LR is converted into a parallel light beam by the collimator 111. Then, the reference light LR is guided to the optical path length changing unit 114 via an optical path length correction member 112 and a dispersion compensation member 113. The optical path length correction member 112 acts so as to match the optical path length of the reference light LR with the optical path length of the measurement light LS. The dispersion compensation member 113 acts so as to match the dispersion characteristics between the reference light LR and the measurement light LS. The optical path length changing unit 114 includes, for example, a corner cube and a movement mechanism for moving the corner cube and can move the corner cube in the incident direction of the reference light LR using the movement mechanism. Thereby, the optical path length of the reference light LR is changed.

The reference light LR that has traveled through the optical path length changing unit 114 passes through the dispersion compensation member 113 and the optical path length correction member 112, is converted from the parallel light beam to the convergent light beam by a collimator 116, and enters an optical fiber 117. The reference light LR that has entered the optical fiber 117 is guided to a polarization controller 118, and the polarization state of the reference light LR is adjusted. Then the reference light LR is guided to an attenuator 120 through an optical fiber 119, and the light amount of the reference light LR is adjusted. After that, the reference light LR is guided to a fiber coupler 122 through an optical fiber 121.

Meanwhile, the measurement light LS generated by the fiber coupler 105 is guided through an optical fiber 127, and is made into a parallel light beam by the collimator lens unit 40. The measurement light LS made into the parallel light beam travels through the optical path length changing unit 41, the optical scanner 42, the OCT focusing lens 43, the mirror 44, and the relay lens 45. The measurement light LS having traveled through the relay lens 45 is reflected by the dichroic mirror 46, is refracted by the objective lens 22, and is irradiated onto the subject's eye E. The measurement light LS is scattered and reflected at various depth positions of the subject's eye E. Returning light of the measurement light LS from the subject's eye E advances in the same path as the forward path in the opposite direction, is guided to the fiber coupler 105, and then reaches the fiber coupler 122 via the optical fiber 128.

The fiber coupler 122 combines (interferes) the measurement light LS incident through the optical fiber 128 and the reference light LR incident through the optical fiber 121 to generate interference light. The fiber coupler 122 splits the interference light at a predetermined splitting ratio (e.g., 1:1) to generate a pair of interference light LC. The pair of interference light LC is guided to a detector 125 through optical fibers 123 and 124, respectively.

The detector 125 is, for example, a balanced photodiode that includes a pair of photodetectors for respectively detecting the pair of interference light LC and outputs the difference between the pair of detection results obtained by the pair of photodetectors. The detector 125 sends the detection result (i.e., interference signal) to the DAQ (data acquisition system) 130. A clock KC is supplied from the light source unit 101 to the DAQ 130. The clock KC is generated in the light source unit 101 in synchronization with the output timing of each wavelength sweeping (scanning) within a predetermined wavelength range performed by the wavelength sweeping type light source. For example, the light source unit 101 optically delays one of the two pieces of branched light obtained by branching the light L0 of each output wavelength, and then generates the clock KC based on the result of the detection of the combined light of the two pieces of branched light. The DAQ 130 performs sampling of the detection result obtained by the detector 125 based on the clock KC. The DAQ 130 sends the result of the sampling of the detection result obtained by the detector 125 to the arithmetic control unit 200. For example, the arithmetic control unit 200 performs the Fourier transform etc. on the spectral distribution based on the detection result obtained by the detector 125 for each series of wavelength scanning (i.e., for each A-line). With this, the reflection intensity profile for each A-line is formed. In addition, the arithmetic control unit 200 forms image data by applying imaging processing to the reflection intensity profiles for the respective A-lines.

The configuration shown in FIG. 1 and FIG. 2 includes both the optical path length changing unit 41 that changes the length of the optical path of the measurement light LS (i.e., measurement optical path or measurement arm) and the optical path length changing unit 114 that changes the length of the optical path of the reference light LR (i.e., reference optical path or reference arm). However, any one of the optical path length changing units 41 and 114 may be provided. The difference between the measurement optical path length and the reference optical path length can be changed by using other optical members.

[Arithmetic Control Unit]

The arithmetic control unit 200 analyzes the detection signals fed from the DAQ 130 to form an OCT image of the subject's eye E. The arithmetic processing therefor is performed in the same manner as in the conventional swept source type OCT apparatus.

In addition, the arithmetic control unit 200 controls each part of the fundus camera unit 2, the display apparatus 3, and the OCT unit 100.

Also, as the control of the fundus camera unit 2, the arithmetic control unit 200 performs following controls: the operation control of the observation light source 11, the operation control of the imaging light source 15 and the operation control of the LEDs 51 and 61; the operation control of the LCD 39; the movement control of the photography focusing lens 31; the movement control of the OCT focusing lens 43; the movement control of the reflection rod 67; the movement control of the focus optical system 60; the movement control of the optical path length changing unit 41; the operation control of the optical scanner 42, and the like.

As the control of the display apparatus 3, the arithmetic control unit 200 controls the display apparatus 3 to display the OCT image of the subject's eye E.

As the control of the OCT unit 100, the arithmetic control unit 200 controls: the operation of the light source unit 101; the operation of the optical path length changing unit 114; the operations of the attenuator 120; the operation of the polarization controllers 103 and 118; the operation of the detector 125; the operation of the DAQ 130; and the like.

As in the conventional computer, the arithmetic control unit 200 includes a processor, RAM, ROM, hard disk drive, and communication interface, for example. A storage device such as the hard disk drive stores a computer program for controlling the ophthalmic apparatus 1. The arithmetic control unit 200 may include various kinds of circuitry such as a circuit board for forming OCT images. In addition, the arithmetic control unit 200 may include an operation device (or an input device) such as a keyboard and a mouse, and a display device such as an LCD.

The fundus camera unit 2, the display apparatus 3, the OCT unit 100, and the arithmetic control unit 200 may be integrally provided (i.e., in a single housing), or they may be separately provided in two or more housings.

[Control System]

Figure 3:
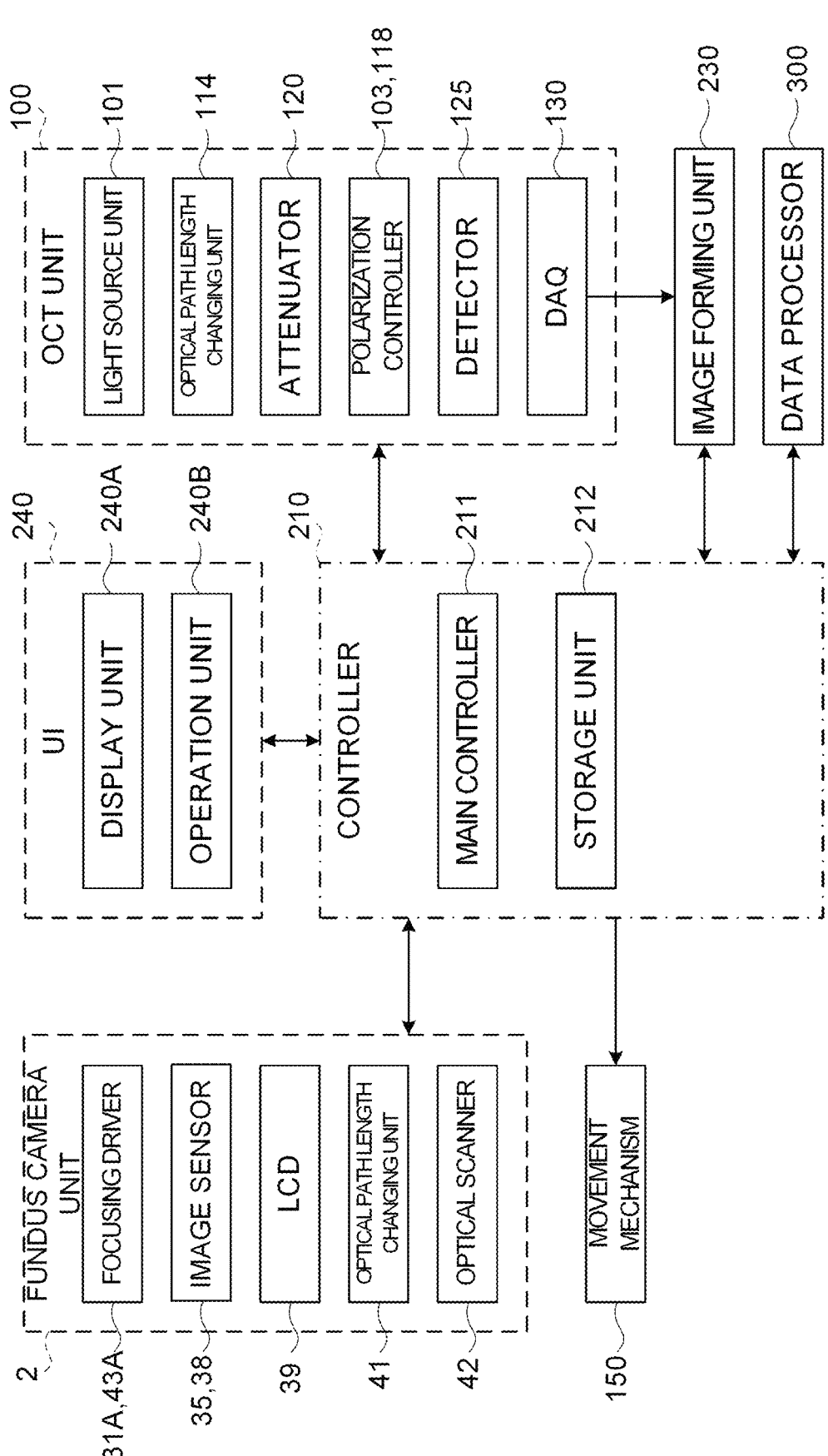
FIG. 3 is a schematic diagram illustrating an example of the configuration of the ophthalmic apparatus according to the first embodiment.

FIG. 3 illustrates an example of a configuration of a control system of the ophthalmic apparatus 1. In FIG. 3, a part of the components included in the ophthalmic apparatus 1 is omitted.

The arithmetic control unit 200 includes a controller 210, and controls each part of the fundus camera unit 2, the display apparatus 3, and the OCT unit 100.

(Controller)

The controller 210 executes various controls. The controller 210 includes a main controller 211 and a storage unit 212.

(Main Controller)

The main controller 211 includes a processor and controls each part of the ophthalmic apparatus 1. For example, the main controller 211 controls components of the fundus camera unit 2 such as focusing drivers 31A and 43A, the image sensors 35 and 38, the LCD 39, the optical path length changing unit 41, the optical scanner 42, and the movement (movement mechanism 150) for moving the optical system. Further, the main controller 211 controls components of the OCT unit 100 such as the light source unit 101, the optical path length changing unit 114, the attenuator 120, the polarization controllers 103 and 118, the detector 125, and the DAQ 130.

For example, the main controller 211 controls the LCD 39 to display the fixation target at a position on the screen of the LCD 39 corresponding to the fixation position set manually or automatically. Moreover, the main controller 211 can change the display position of the fixation target displayed on the LCD 39 (in a continuous manner or in a phased manner). Thereby, the fixation target can be moved (that is, the fixation position can be changed). The display position of the fixation target and movement mode of the fixation target are set manually or automatically. Manual setting is performed using GUI, for example. Automatic setting is performed by the data processor 300, for example.

The focusing driver 31A moves the photography focusing lens 31 in an optical axis direction of the imaging optical system 30, and moves the focus optical system 60 in an optical axis direction of the illumination optical system 10. As a result, the focusing position of the imaging optical system 30 is changed. In some embodiments, the focusing driver 31A includes a dedicated mechanism for moving the photography focusing lens 31 and a dedicated mechanism for moving the focus optical system 60. The focusing driver 31A is controlled when performing focus adjustment or the like.

The focusing driver 43A moves the OCT focusing lens 43 in an optical axis direction of the measurement optical path. As a result, the focusing position of the measurement light LS is changed. For example, the focus position of the measurement light LS can be arranged at the fundus Ef or near the fundus Ef by moving the OCT focusing lens 43 to the first lens position. For example, the focus position of the measurement light LS can be arranged at a far point position by moving the OCT focusing lens 43 to the second lens position. The focus position of the measurement light LS corresponds to the depth position (z position) of the beam waist of the measurement light LS.

The movement mechanism 150 three-dimensionally moves at least the fundus camera unit 2 (optical system), for example. In a typical example, the movement mechanism 150 includes a mechanism for moving at least the fundus camera unit 2 in the x direction (left-right direction), a mechanism for moving it in the y direction (up-down direction), and a mechanism for moving it in the z direction (depth direction, front-back direction). The mechanism for moving in the x direction includes a x stage movable in the x direction and a x movement mechanism for moving the x stage, for example. The mechanism for moving in the y direction includes a y stage movable in the y direction and a y movement mechanism for moving the y stage, for example. The mechanism for moving in the z direction includes a z stage movable in the z direction and a z movement mechanism for moving the z stage, for example. Each movement mechanism includes an actuator such as a pulse motor, and operates under the control of the main controller 211.

The control for the movement mechanism 150 is used for alignment and tracking. Here, tracking is to move the optical system of the apparatus according to the movement of the subject's eye E. To perform tracking, alignment and focus adjustment are performed in advance. The tracking is a function of maintaining a suitable positional relationship in which alignment and focusing are matched by causing the position of the optical system of the apparatus and the like to follow the eye movement. In some embodiments, the movement mechanism 150 is configured to be controlled to change the optical path length of the reference light (that is, the difference of the optical path length between the optical path of the measurement light and the optical path of the reference light).

In the case of manual alignment, a user operates a user interface (UI) 240 described below to relatively move the optical system and subject's eye E so as to cancel the displacement of the subject's eye E with respect to the optical system. For example, the main controller 211 controls the movement mechanism 150 to relatively move the optical system and the subject's eye E by outputting a control signal corresponding to the operation content with respect to the user interface 240 to the movement mechanism 150.

In the case of automatic alignment, the main controller 211 controls the movement mechanism 150 to relatively move the optical system and the subject's eye E so as to cancel the displacement of the subject's eye E with respect to the optical system. In some embodiments, the main controller 211 controls the movement mechanism 150 to relatively move the optical system and the subject's eye E by outputting a control signal to the movement mechanism 150 so that the optical axis of the optical system substantially coincides with the axis of the subject's eye E and the distance of the optical system with respect to the subject's eye E is a predetermined working distance. Here, the working distance is a preset value which is called a working distance of the objective lens 22, and it means the distance between the subject's eye E and the optical system when measuring (imaging) using the optical system.

The main controller 211 controls the fundus camera unit 2 etc. to control the fundus imaging (photography) and the anterior segment imaging. Further, the main controller 211 controls the fundus camera unit 2 and the OCT unit 100 etc. to control the OCT measurement. The main controller 211 is capable of performing a plurality of preliminary operations prior to OCT measurement. Examples of the preliminary operation include alignment, rough focus adjustment, polarization adjustment, and fine focus adjustment. The plurality of preliminary operations is performed in a predetermined order. In some embodiments, the plurality of preliminary operations is performed in an order described above.

It should be noted that the types and the orders of the preliminary operations are not so limited, and they may be optional. For example, the preliminary operations may further include microcoria judgment. The microcoria judgment is a preliminary operation to judge whether the pupil of the subject's eye E is small or not (whether the subject's eye E is microcoria or not). The microcoria judgment may be performed between the rough focus adjustment and the optical path length difference adjustment. In some embodiments, the microcoria judgment includes, for example, a series of processes as follows: acquiring the front image (anterior segment image) of the subject's eye E; identify an image region corresponding to the pupil; calculating the size (e.g., diameter, circumference length) of the pupil region; judging whether the pupil of the subject's eye E is microcoria or not based on the calculated size (threshold processing); and controlling the diaphragm 19 when judged that the pupil of the subject's eye E is microcoria. In some embodiments, the calculation of the size of the pupil region includes processing of circularly or to elliptically approximating the pupil region.

The rough focus adjustment is a kind of focus adjustment using the split indicator. The rough focus adjustment may be performed by determining the position of the photography focusing lens 31 based on information, which is obtained by associating the eye refractive power acquired in advance with the position of the photography focusing lens 31, and a measured value of the refractive power of the subject's eye E.

The fine focus adjustment is performed on the basis of interference sensitivity of OCT measurement. For example, the fine focus adjustment can be performed by: monitoring interference intensity (interference sensitivity) of interference signal acquired by performing OCT measurement of the subject's eye E; searching the position of the OCT focusing lens 43 so as to maximize the interference intensity; and moving the OCT focusing lens 43 to the searched position.

To perform the optical path length difference adjustment, the optical system is controlled so that a predetermined position on the subject's eye E is a reference position of a measurement range in the depth direction. The control is performed on at least one of the optical path length changing units 41 and 114. Thereby, the difference of the optical path length between the measurement optical path and the reference optical path is adjusted. By setting the reference position in the optical path length difference adjustment, OCT measurement can be performed with high accuracy over a desired measurement range in the depth direction simply by changing the wavelength sweep speed.

To perform the polarization adjustment, the polarization state of the reference light LR is adjusted for optimizing the interference efficiency between the measurement light LS and the reference light LR.

(Storage Unit)

The storage unit 212 stores various types of data. Examples of the data stored in the storage unit 212 include image data of an OCT image, image data of the fundus image, image data of the anterior segment image, and subject's eye information. The subject's eye information includes information on the subject such as patient ID and name, and information on the subject's eye such as identification information of the left eye/right eye.

In addition, the storage unit 212 stores various kinds of computer programs and data for operating the ophthalmic apparatus 1.

The controller 210 can control an image forming unit 230 and a data processor 300.

(Image Forming Unit)

The image forming unit 230 forms an OCT image (image data) of the subject's eye E based on the sampling data obtained by sampling the detection signal from the detector 125 using the DAQ 130. Examples of the OCT image formed by the image forming unit 230 include an A-scan (A-mode) image, a B-scan (B-mode) image (tomographic image), a C-scan (C-mode) image, and the like. As with the conventional swept source OCT, the image formation process includes noise removal (noise reduction), filtering, dispersion compensation, fast Fourier transform (FFT), and the like. In the case of employing an OCT apparatus of another type, the image forming unit 230 performs known processing according to the type employed.

The image forming unit 230 includes, for example, the circuitry described above. It should be noted that "image data" and an "image" based on the image data may not be distinguished from each other in the present specification.

(Data Processor)

The data processor 300 processes data acquired through imaging of the subject's eye E or data acquired through OCT measurement. For example, the data processor 300 performs various kinds of image processing and various kinds of analysis processing on the image formed by the image forming unit 230. Specifically, the data processor 300 performs various types of image correction processing such as brightness correction. The data processor 300 performs various kinds of image processing and various kinds of analysis processing on images captured by the fundus camera unit 2 (e.g., fundus images, anterior segment images, etc.).

The data processor 300 performs known image processing such as interpolation for interpolating pixels in tomographic images to form image data of the three-dimensional image of the fundus Ef or the anterior segment Ea. It should be noted that the image data of the three-dimensional image means image data in which the positions of pixels are defined in a three-dimensional coordinate system. Examples of the image data of the three-dimensional image include image data defined by voxels three-dimensionally arranged. Such image data is referred to as volume data or voxel data. When displaying an image based on volume data, the data processor 300 performs rendering (volume rendering, maximum intensity projection (MIP), etc.) on the volume data, thereby forming image data of a pseudo three-dimensional image viewed from a particular line of sight. The pseudo three-dimensional image is displayed on the display device such as a display unit 240A.

The three-dimensional image data may be stack data of a plurality of tomographic images. The stack data is image data formed by three-dimensionally arranging tomographic images along a plurality of scan lines based on positional relationship of the scan lines. That is, the stack data is image data obtained by representing tomographic images, which are originally defined in their respective two-dimensional coordinate systems, by a single three-dimensional coordinate system. That is, the stack data is image data formed by embedding tomographic images into a single three-dimensional space.

The data processor 300 can form a B-mode image (longitudinal cross-sectional image, axial cross-sectional image) in an arbitrary cross section, a C-mode image (transverse section image, horizontal cross-sectional image) in an arbitrary cross section, a projection image, a shadowgram, etc., by performing various renderings on the acquired three-dimensional data set (volume data, stack data, etc.). An image in an arbitrary cross section such as a B-mode image or a C-mode image is formed by selecting pixels (voxels) on a designated cross section from the three-dimensional data set. The projection image is formed by projecting the three-dimensional data set in a predetermined direction (z direction, depth direction, axial direction). The shadowgram is formed by projecting a part of the three-dimensional data set in a predetermined direction. Examples of the part of the three-dimensional data set include partial data corresponding to a specific layer. An image having a viewpoint on the front side of the subject's eye, such as the C-mode image, the projection image, and the shadowgram, is called a front image (en-face image).

The data processor 300 can build (form) the B-mode image or the front image (blood vessel emphasized image, angiogram) in which retinal blood vessels and choroidal blood vessels are emphasized (highlighted), based on data (for example, B-scan image data) acquired in time series by OCT. For example, the OCT data in time series can be acquired by repeatedly scanning substantially the same site of the subject's eye E.

In some embodiments, the data processor 300 compares the B-scan images in time series acquired by B-scan for substantially the same site, converts the pixel value of a change portion of the signal intensity into a pixel value corresponding to the change portion, and builds the emphasized image in which the change portion is emphasized. Further, the data processor 300 forms an OCTA image by extracting information of a predetermined thickness at a desired site from a plurality of built emphasized images and building as an en-face image.

An image (for example, a three-dimensional image, a B-mode image, a C-mode image, a projection image, a shadowgram, and an OCTA image) generated by the data processor 300 is also included in the OCT image.

Further, the data processor 300 determines the focus state of the measurement light LS in fine focus adjustment control by analyzing the detection result of the interference light obtained by the OCT measurement. For example, the main controller 211 performs repetitive OCT measurements while controlling the focusing driver 43A according to a predetermined algorithm. The data processor 300 analyzes detection results of interference light LC repeatedly acquired by the OCT measurements to calculate predetermined evaluation values relating to image quality of OCT images. The data processor 300 determines whether the calculated evaluation value is equal to or less than a threshold. In some embodiments, the fine focus adjustment is continued until the calculated evaluation value becomes equal to or less than the threshold. That is, when the evaluation value is equal to or less than the threshold, it is determined that the focus state of the measurement light LS is appropriate. And the fine focus adjustment is continued until it is determined that the focus state of the measurement light LS is appropriate.

In some embodiments, the main controller 211 monitors the intensity of the interference signal (interference intensity, interference sensitivity) acquired sequentially while acquiring the interference signal by performing the repetitive OCT measurements as described above. In addition, while performing this monitoring process, the OCT focusing lens 43 is moved to find the position of the OCT focusing lens 43 in which the interference intensity is maximized. With the fine focus adjustment thus performed, the OCT focusing lens 43 can be guided to the position where the interference intensity is optimized.

Further, the data processor 300 determines the polarization state of at least one of the measurement light LS and the reference light LR by analyzing the detection result of the interference light obtained by the OCT measurement. For example, the main controller 211 performs repetitive OCT measurements while controlling at least one of the polarization controllers 103 and 118 according to a predetermined algorithm. In some embodiments, the main controller 211 controls the attenuator 120 to change an attenuation of the reference light LR. The data processor 300 analyzes detection results of interference light LC repeatedly acquired by the OCT measurements to calculate predetermined evaluation values relating to image quality of OCT images. The data processor 300 determines whether the calculated evaluation value is equal to or less than a threshold. The threshold is set in advance. Polarization adjustment is continued until the calculated evaluation value becomes equal to or less than the threshold. That is, when the evaluation value is equal to or less than the threshold, it is determined that the polarization state of the measurement light LS is appropriate. And the polarization adjustment is continued until it is determined that the polarization state of the measurement light LS is appropriate.

In some embodiments, the main controller 211 can monitor the interference intensity also in the polarization adjustment.

The data processor 300 according to the embodiments determines whether or not the image formed by the image forming unit 230 or the data processor 300 is an analysis error image including a predetermined analysis error factor. This allows to automatically determine whether or not re-imaging (re-acquisition, re-measurement) is necessary based on certain determination criteria.

Figure 4:
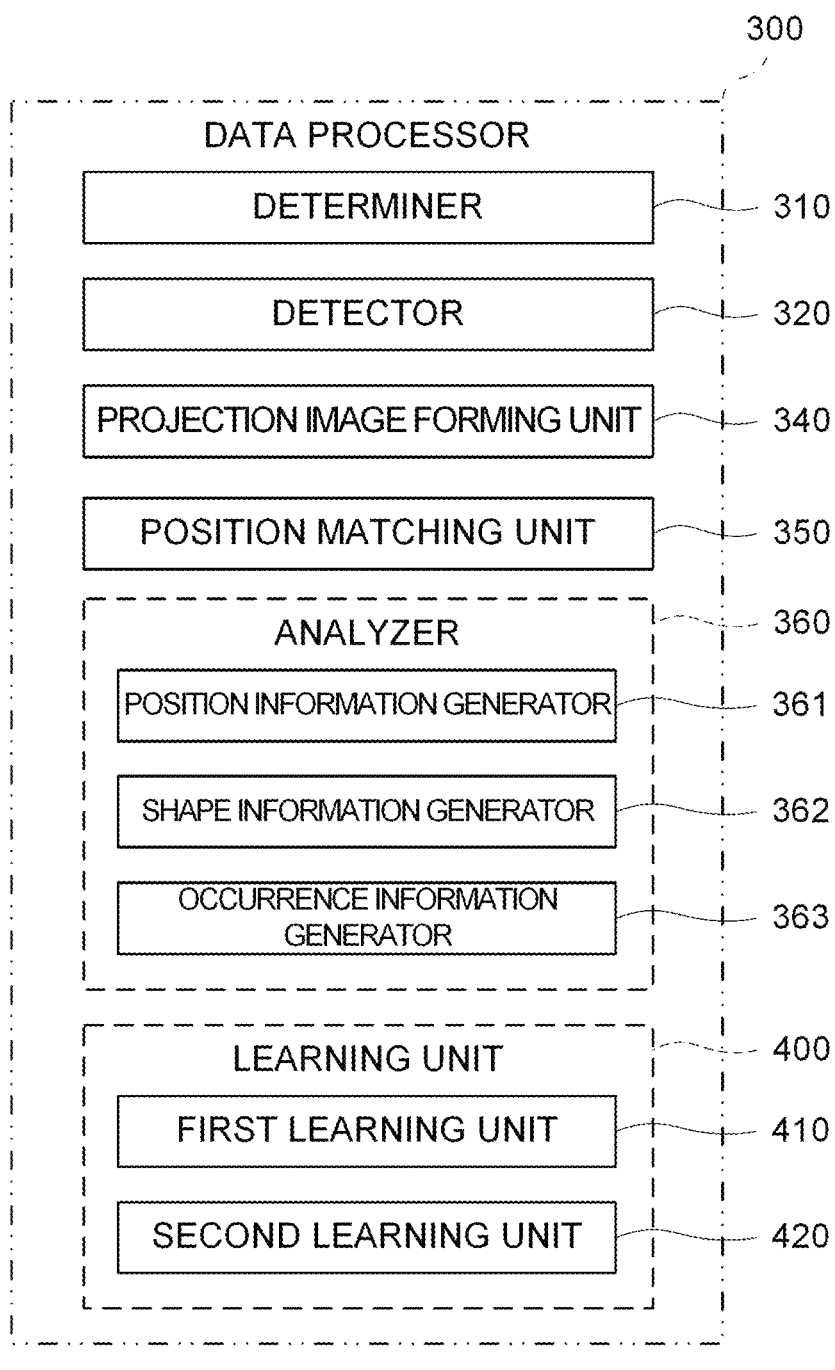
FIG. 4 is a schematic diagram illustrating an example of the configuration of the ophthalmic apparatus according to the first embodiment.
Figure 5:
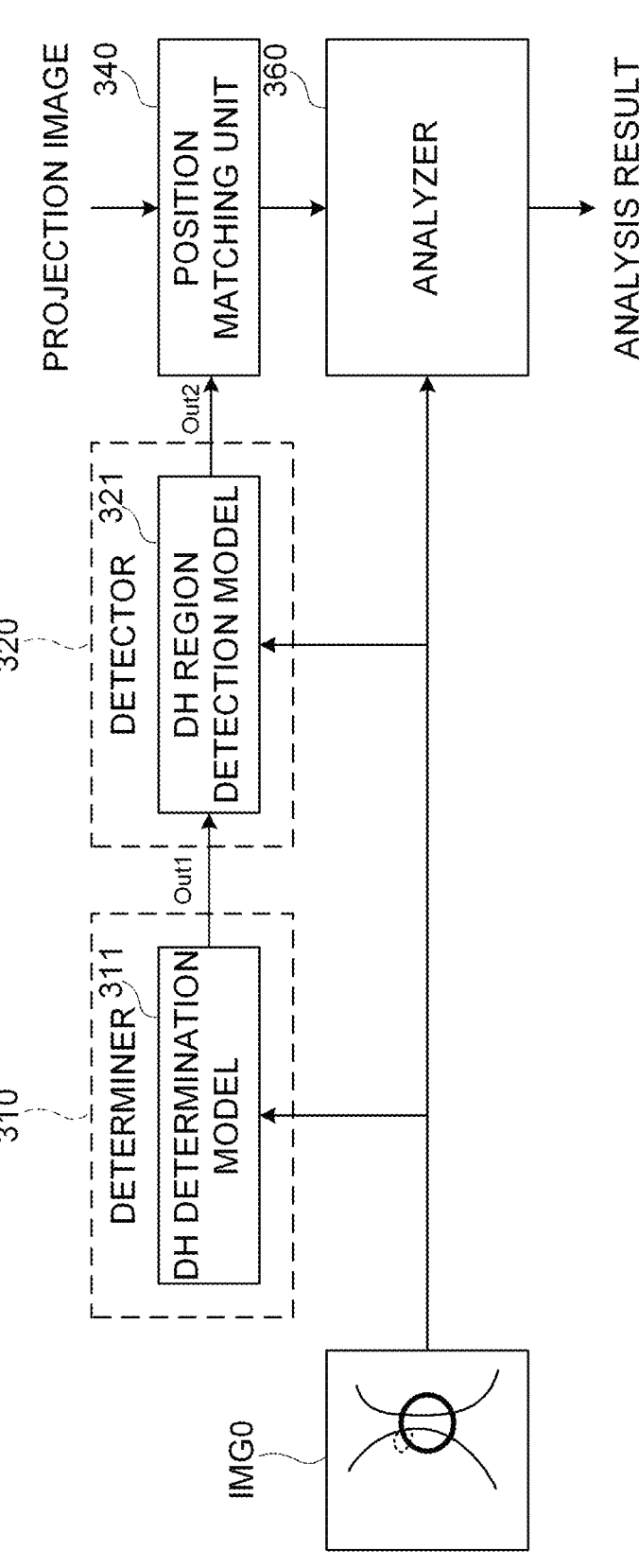
FIG. 5 is a schematic diagram for explaining an example of an operation of the ophthalmic apparatus according to the first embodiment.
Figure 6:
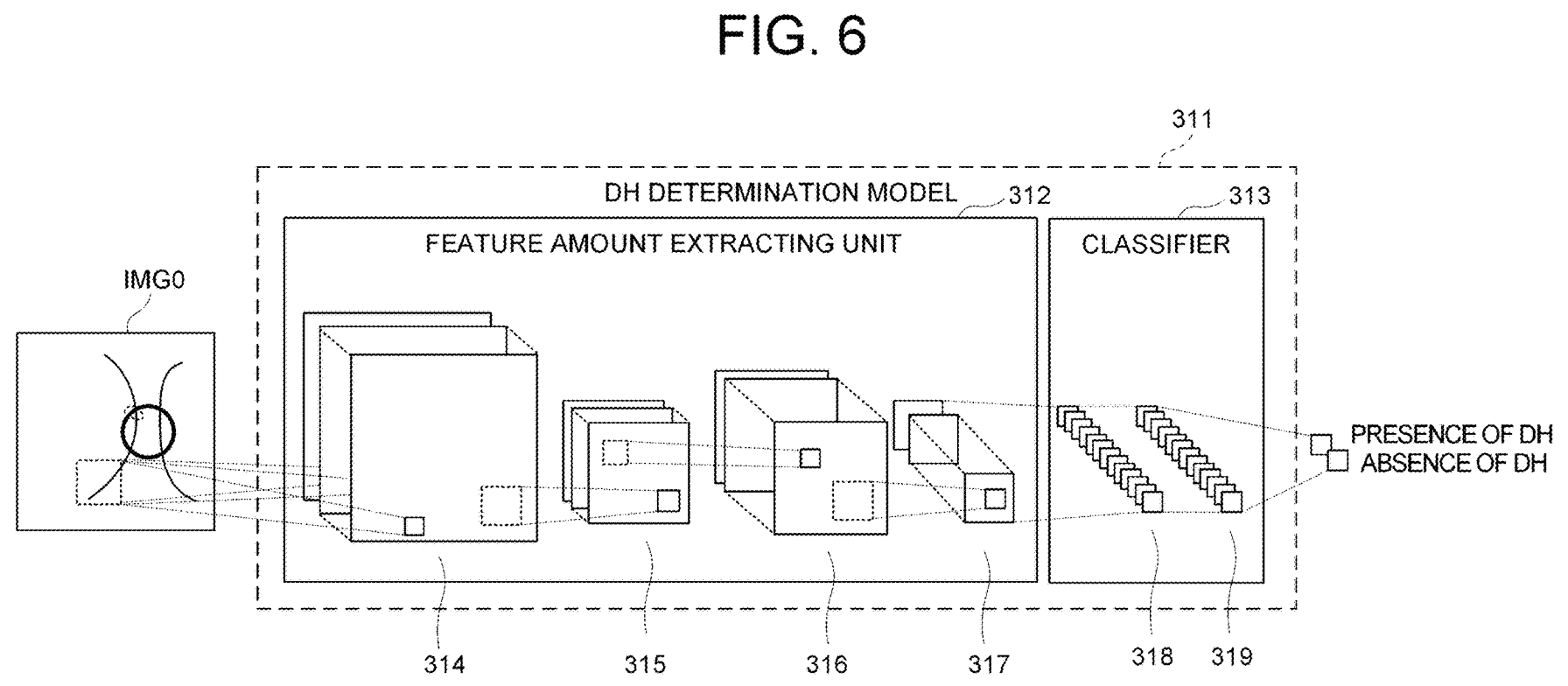
Figure 7:
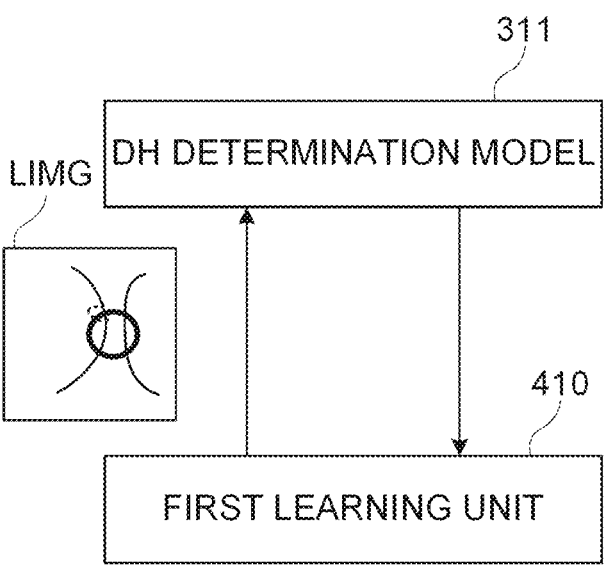
FIG. 7 is a schematic diagram for explaining an operation of the ophthalmic apparatus according to the first embodiment.
Figure 8:
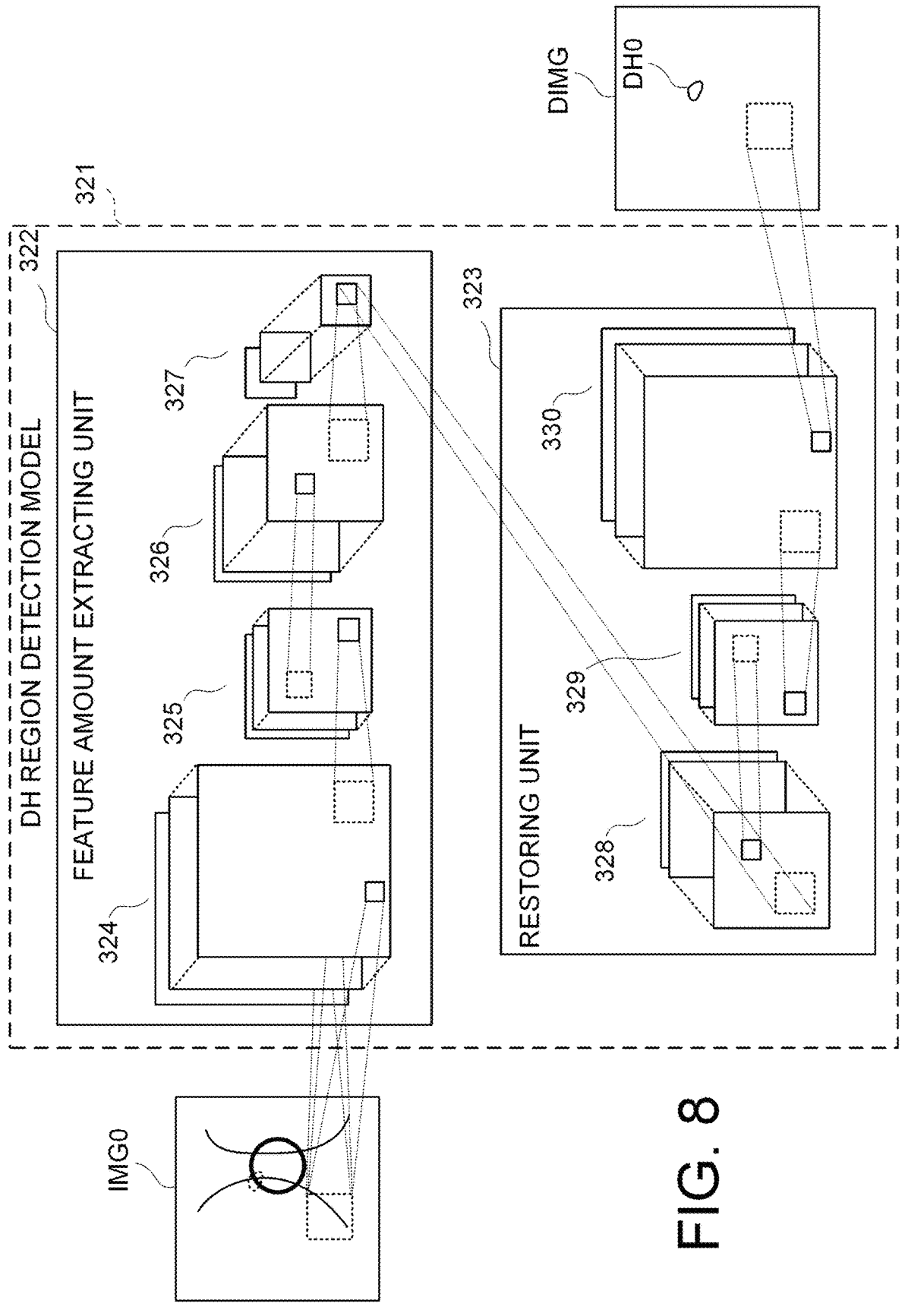
FIG. 8 is a schematic diagram illustrating an example of the configuration of the ophthalmic apparatus according to the first embodiment.
Figure 9:
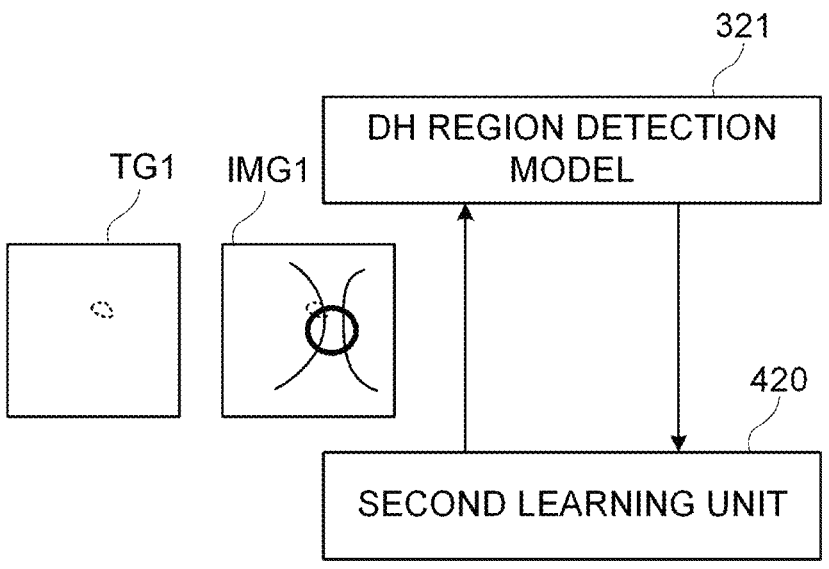
FIG. 9 is a schematic diagram for explaining an operation of the ophthalmic apparatus according to the first embodiment.
Figure 10:
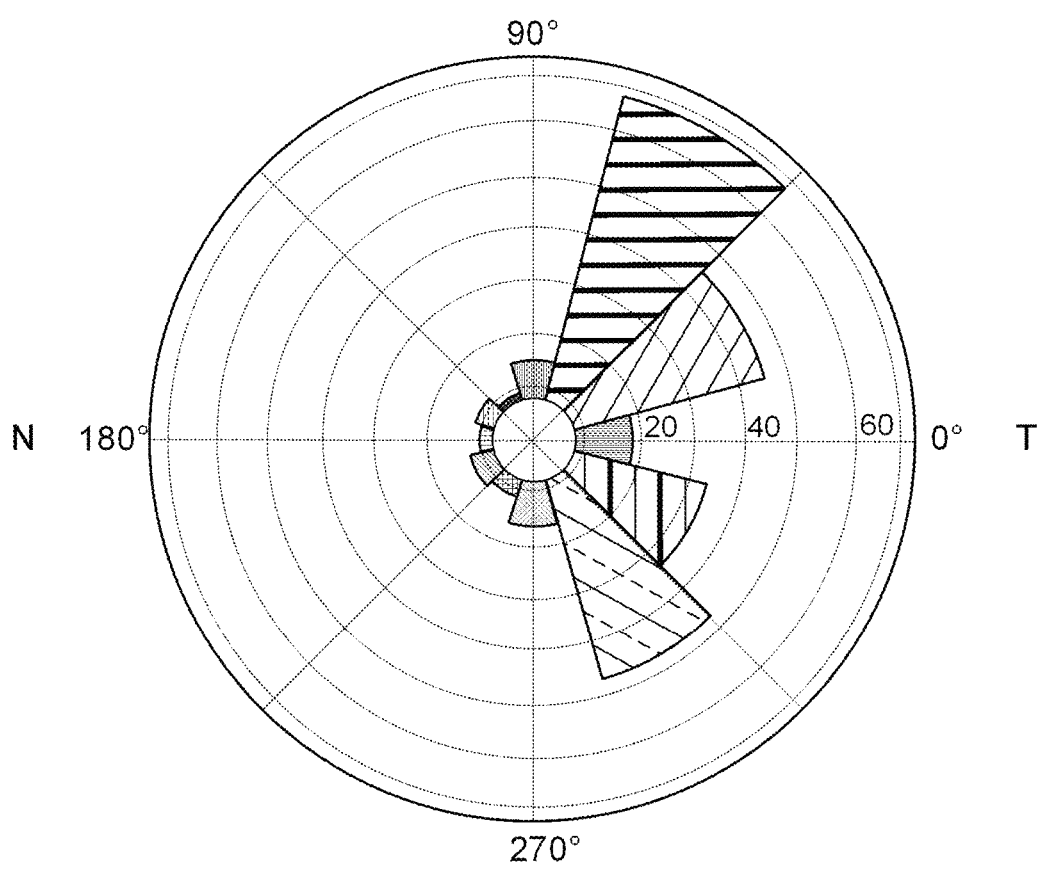
FIG. 10 is a schematic diagram for explaining an operation of the ophthalmic apparatus according to the first embodiment.
Figure 11:
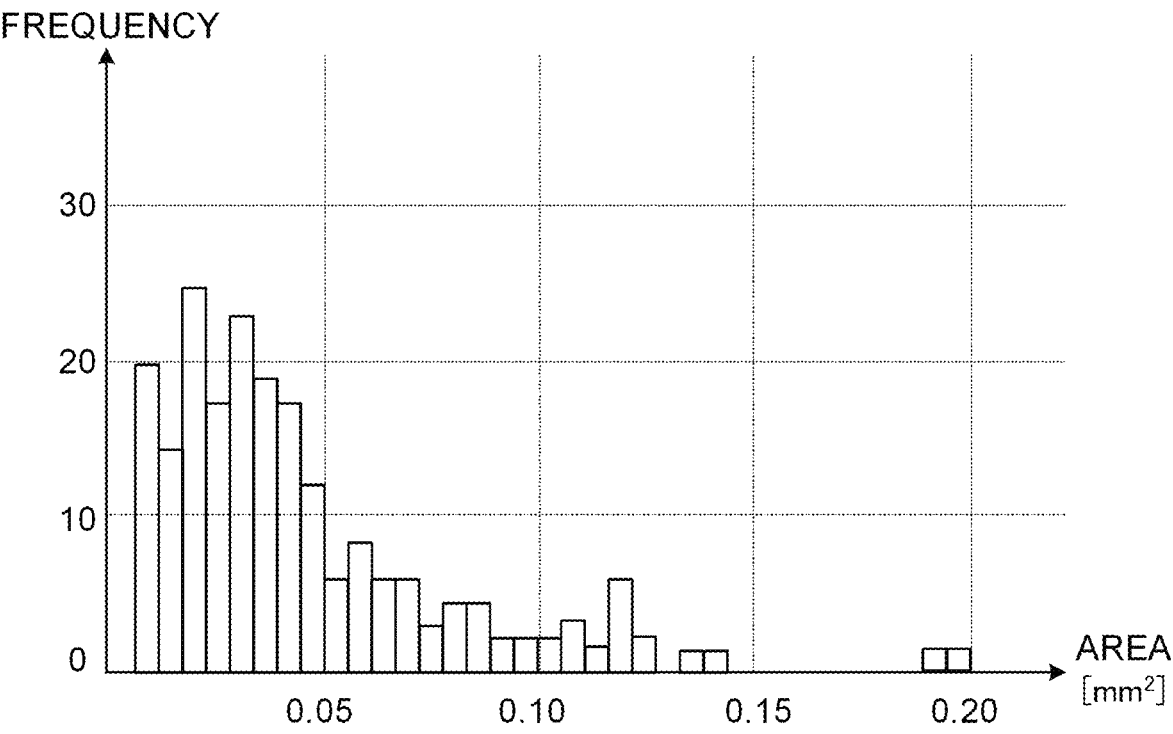
FIG. 11 is a schematic diagram for explaining an operation of the ophthalmic apparatus according to the first embodiment.

FIGS. 4 to 11 show diagrams for explaining the data processor 300 according to the embodiments. FIG. 4 represents a block diagram of an example of the configuration of the data processor 300 according to the embodiments. FIG. 5 represents a schematic diagram for explaining an operation of the data processor 300 in FIG. 4. FIG. 6 represents an example of a configuration of a disc hemorrhage (DH) determination model 311 in FIG. 5. FIG. 7 represents a schematic diagram for explaining machine learning for the DH determination model 311 performed by a first learning unit 410 in FIG. 4. FIG. 8 represents an example of a configuration of a disc hemorrhage (DH) region detection model 321 in FIG. 5. FIG. 9 represents a schematic diagram for explaining machine learning for the DH region detection model 321 performed by a second learning unit 420 in FIG. 4. FIGS. 10 and 11 represent schematic diagrams for explaining an operation of an analyzer 360 in FIG. 5.

In addition to the data processing described above, the data processor 300 can detect a disc hemorrhage (DH) region in the fundus image (e.g., the captured images described above) of the subject's eye E acquired using the fundus camera unit 2, and can generate analysis information for the detected DH region(s). Such the data processor 300 includes a determiner 310, a detector 320, a projection image forming unit 340, a position matching unit 350, an analyzer 360, and a learning unit 400. The learning unit 400 may not be included in the data processor 300.

As shown in FIG. 5, the determiner 310 determines the presence or absence of the DH for the fundus image IMG0 that is acquired using the fundus camera unit 2, using the DH determination model 311 obtained by performing machine learning. The detector 320 detects the DH region in the fundus image IMG0 that is determined to have the DH by the determiner 310, using the DH region detection model 321 obtained by performing machine learning. The projection image forming unit 340 forms a projection image based on the OCT data acquired by performing OCT measurement using the OCT unit 100 on the subject's eye E that the fundus image IMG0 has been acquired. The position matching unit 350 performs position matching between the fundus image IMG0 that the DH region has been detected and the projection image as the OCT data.

The analyzer 360 generates position information of the DH region, shape information of the DH region, and occurrence information of the DH region, by analyzing the fundus image that the position matching has been performed with the projection image (i.e., OCT data defined in the OCT coordinate system) by the position matching unit 350. Such the analyzer 360 includes a position information generator 361, a shape information generator 362, and an occurrence information generator 363. The position information generator 361 generates the position information of the DH region. The shape information generator 362 generates the shape information of the DH region. The occurrence information generator 363 generates the occurrence information of the DH region.

The learning unit 400 generates the DH determination model 311 and the DH region detection model 321 by performing machine learning. The learning unit 400 includes the first learning unit 410 and the second learning unit 420. The first learning unit 410 generates the DH determination model 311 by performing machine learning. The second learning unit 420 generates the DH region detection model 321 by performing machine learning.

(Determiner)

The determiner 310 determines the presence or absence of the DH for fundus image IMG0 using the DH determination model 311 that is a learned model obtained by performing machine learning in advance.

The learned model according to the embodiments is used in the computer (processor) including a CPU and a memory. The function of the determiner 310 is realized by a Convolutional Neural Network (Hereinafter, CNN), for example. That is, in accordance with the commands from the learned model stored in the memory, the CPU operates so as to perform the calculation based on the learned weighting coefficients and response functions in the CNN on the pixel values of the fundus image that is input to a convolution layer 314 of a feature amount extracting unit 312 described below, and to output a determination result (classification result) from a classifier 313 described below. The determiner 310 having such a configuration can extract a local correlation pattern while gradually reducing the resolution of the fundus image, and can output the determination result based on the extracted correlation pattern.

As shown in FIG. 6, the DH determination model 311 (determiner 310) includes the feature amount extracting unit 312 and the classifier 313. The feature amount extracting unit 312 repeats the extraction of the feature amount and the downsampling (filtering) for each predetermined image region for the input fundus image IMG0, and extracts the feature amount of the fundus image. The classifier 313 generates output information indicating the presence or absence of the DH based on the feature amount extracted by the feature amount extracting unit 312, and outputs information Out1 (the presence of DH/absence of DH) indicating whether or not the fundus image IMG0 has the DH based on the generated output information.

The feature amount extracting unit 312 includes a plurality of units in which units are connected in a plurality of stages. Each unit includes a convolution layer and a pooling layer. In each unit, the inputs of the pooling layer are connected to the outputs of the convolution layer. The pixel values of the corresponding pixels in the fundus image are input to the inputs of the convolution layer in the first stage. The inputs of the convolution layer in the latter stage are connected to the outputs of the pooling layer in the previous stage.

In FIG. 6, the feature amount extracting unit 312 includes two units connected in two stages. That is, in the feature amount extracting unit 312, the unit including the convolution layer 316 and the pooling layer 317 is connected to the subsequent stage of the unit including the convolution layer 314 and the pooling layer 315. The outputs of the pooling layer 315 are connected to the inputs of the convolution layer 316.

The classifier 313 includes fully connected layers 318 and 319. The outputs of the fully connected layer 318 are connected to the inputs of the fully connected layer 319.

In the feature amount extracting unit 312 and the classifier 313, learned weighting coefficients (learning parameters) are assigned between the neurons in the connected two layers. The weighting coefficients are updated by performing machine learning. Each neuron performs calculation using a response function on calculation result in which weighting coefficient(s) from one or more input neurons is/are added, and outputs the obtained calculation result to a neuron in the next stage.

As shown in FIG. 7, the first learning unit 410 generates the DH determination model 311 with updated weighting coefficients for an existing initial model by performing known machine learning on the initial model using the fundus image LIMG with a label indicating the presence or absence of the DH as teaching data. The existing weighting coefficients are updated by performing machine learning using the fundus image LIMG with a label indicating the presence or absence of the DH as the teaching data. The teaching data may be a plurality of pairs of data, each pair consisting of a fundus image and label information indicating whether or not the DH is depicted in the fundus image. The presence or absence of the DH is determined in advance for each fundus image based on the result(s) of judgment by the doctor(s), and is assigned as a label on the fundus image. The first learning unit 410 can further learn (train) the DH determination model 311 by performing machine learning on the generated DH determination model 311 using further different teaching data.

That is, the first learning unit 410 generates the DH determination model 311 that is a learned model for determining (classifying) whether or not the DH is depicted in the fundus image of the subject's eye E, by performing known supervised learning (machine learning) using a plurality of fundus images LIMG as training data. The machine learning may be unsupervised learning or reinforcement learning. In some embodiments, the weighting coefficient(s) is/are updated by transfer learning.

The DH determination model 311 (feature amount extracting unit 312) may have a known layer structure such as VGG16, VGG19, InceptionV3, ResNet18, ResNet50, Xception, DenseNet201. The classifier 313 may have a configuration such as random forest, support vector machine (SVM). For example, the DH determination model 311 according to the first embodiment is built using DenseNet201.

(Detector)

The detector 320 detects the DH region in the fundus image IMG0 that is determined to have the DH by the determiner 310, using the DH region detection model 321 that is a learned model obtained by performing machine learning in advance.

The learned model according to the embodiments is used in the computer (processor) including a CPU and a memory. The function of the detector 320 is realized, for example, by the CNN. That is, in accordance with the commands from the learned model stored in the memory, the CPU operates so as to perform the calculation based on the learned weighting coefficients and response functions in the CNN on the pixel values of the fundus image that is input to a convolution layer 324 of a feature amount extracting unit 322 described below, and to output an image that the detected DH region is depicted from a restoring unit 323 described below. The detector 320 having such a configuration can extract local correlation pattern(s) while gradually reducing the resolution of the fundus image by a convolution operation, and can output a detection image corresponding to the fundus image by an inverse convolution operation from the extracted correlation pattern(s).

As shown in FIG. 8, the DH region detection model 321 (detector 320) includes a feature amount extracting unit 322 and the restoring unit 323. The feature amount extracting unit 322 repeats the extraction of the feature amount and the downsampling (filtering) for each predetermined image region for the input fundus image IMG0, and extracts the feature amount of the fundus image. The restoring unit 323 repeatedly restores the image corresponding to the feature amount for each predetermined image region for the feature amount extracted by the feature amount extracting unit 322, and outputs a detection image Out2 (see FIG. 5) corresponding to the feature amount. The detected DH region is depicted in the detection image Out2. In FIG. 8, the detection image Out2 is the output image (DH region detection image) DIMG in which the DH region DH0 is depicted.

Similar to the feature amount extracting unit 312, the feature amount extracting unit 322 includes a plurality of units in which units are connected in a plurality of stages. Each unit includes a convolution layer and a pooling layer. In each unit, the inputs of the pooling layer are connected to the outputs of the convolution layer. The pixel values of the corresponding pixels in the fundus image are input to the inputs of the convolution layer in the first stage. The inputs of the convolution layer in the latter stage are connected to the outputs of the pooling layer in the previous stage.

In FIG. 8, the feature amount extracting unit 322 includes two units connected in two stages. That is, in the feature amount extracting unit 322, the unit including the convolution layer 326 and the pooling layer 327 is connected to the subsequent stage of the unit including the convolution layer 324 and the pooling layer 325. The outputs of the pooling layer 325 are connected to the inputs of the convolution layer 326.

The restoring unit 323 includes one or more units each of which includes an inverse convolution layer and a pooling layer. The one or more units are connected in one or more stages. In each unit, the output of the inverse convolution layer is connected to the input of the pooling layer. The inputs of the inverse convolution layer in the first stage are connected to the outputs of the pooling layer in the feature amount extracting unit 322. The inputs of the inverse convolution layer in the latter stage are connected to the outputs of the pooling layer in the previous stage.

In FIG. 8, the restoring unit 323 includes an inverse convolution layer 328 corresponding to the pooling layer 327 of the feature amount extracting unit 322 and one unit. In other words, in the restoring unit 323, the unit including the pooling layer 329 and the inverse convolution layer 330 is connected to the second stage of the inverse convolution layer 328 corresponding to the pooling layer 327. The outputs of the pooling layer 329 are connected to the input of the inverse convolution layer 330.

Similar to the DH determination model 311, the learned weighting coefficients (learning parameters) are assigned between neurons in the two connected layers in the feature amount extracting unit 322 and the restoring unit 323. Each neuron performs calculation using a response function on calculation result in which weighting coefficient(s) from one or more input neurons is/are added, and outputs the obtained calculation result to a neuron in the next stage.

As shown in FIG. 9, the second learning unit 420 generates the DH region detection model 321 with updated weighting coefficients for an existing initial model by performing known machine learning on the initial model using a plurality of pairs of image groups as teaching data. Each pair consists of a fundus image IMG1 and a DH region image TG1 representing the DH region depicted in the fundus image IMG1. The existing weighting coefficients are updated by performing machine learning using the plurality of pairs of image groups as the teaching data. The DH region image is generated based on the result(s) of judgment by the doctor(s) for each fundus image. For example, the DH region image TG1 is generated by designating a boundary of the DH region in the fundus image IMG1 using the operation unit 240B by the doctor. The second learning unit 420 can further learn (train) the DH region detection model 321 by performing machine learning on the generated DH region detection model 321 using further different teaching data.

That is, the second learning unit 420 generates the DH region detection model 321 that is a learned model for detecting the DH region in the fundus image by performing known supervised learning (machine learning) using a plurality of pairs of image groups (fundus image IMG1, DH region image TG1) as training data. The machine learning may be unsupervised learning or reinforcement learning. In some embodiments, the weighting coefficient(s) is/are updated by transfer learning.

Here, the teaching data (second teaching data) used for learning the DH region detection model 321 by the second learning unit 420 includes at least part of the teaching data (first teacher data) used for learning the DH determination model 311 by the first learning unit 410. That is, the teaching data used for learning the DH region detection model 321 by the second learning unit 420 includes the fundus image included in the teaching data used for learning the DH determination model 311 by the first learning unit 410. This allows to improve the accuracy of the DH region detection as described below, without increasing the amount of teaching data, compared to the case where a single learned model is used to detect the DH region.

The DH region detection model 321 (detector 320) may have a known layer structure such as VGG16, VGG19, InceptionV3, ResNet18, ResNet50, Xception, U-Net, ResU-net, ResUnet++. For example, the DH region detection model 321 according to the first embodiment is built by ResUnet++(Debesh Jha et al., "ResUnet++: An Advanced Architecture for Medical Image Segmentation", 21st IEEE International Symposium on Multimedia, December 2019).

(Projection Image Forming Unit)

The projection image forming unit 340 forms the projection image of the fundus Ef of the subject's eye E as described above. For example, the projection image forming unit 340 forms the projection image by projecting the volume data of the fundus Ef of the subject's eye E in the z direction.

(Position Matching Unit)

The position matching unit 350 performs position matching between the fundus image that the DH region has been detected and the projection image formed by the projection image forming unit 340. The fundus image on which the position matching is performed by the position matching unit 350 is a fundus image in which the DH region detected by the detector 320 is depicted. This enables the position of each pixel in the fundus image on which the position matching has been performed by the position matching unit 350 to correspond to the position in the OCT coordinate system.

In some embodiments, the position matching unit 350 performs position matching so that a position corresponding to the optical axis of the OCT unit 100 (interference optical system) in the projection image and a position corresponding to the optical axis of the fundus camera unit 2 (imaging optical system) in the fundus image are coincided.

In some embodiments, the position matching unit 350 identifies a characteristic site in the projection image and a characteristic site in the fundus image, and performs position matching so that the positions of the both characteristic sites in the both images are coincided. In this case, for example, the region(s) may be automatically or manually corrected so that a region corresponding to an optic disc in the fundus image coincides with a region corresponding to an optic disc in the projection image. Since the characteristic site can be identified with high precision from the tomographic structure of the fundus using the OCT data, the boundary of the region corresponding to the optic disc that is difficult to discriminate from the fundus image alone can be detected with high precision.

In some embodiments, the position matching unit 350 perform affine transform on at least one of the fundus image and the projection image when performing position matching between the fundus image and the projection image. For example, the affine transform is performed on the projection image along with the coordinate system.

The OCT data acquired by performing OCT measurement is data with high reproducibility and data that enables to identify the position and shape of the optic disc with high precision. As a result, the analysis result of the DH region obtained by the analyzer 360 described below can also be obtained with high reproducibility and high precision.

(Analyzer)

The analyzer 360 generates the position information of the DH region, the shape information of the DH region, and the occurrence information of the DH region, by analyzing the fundus image on which the position matching has been performed with the projection image by the position matching unit 350. Specifically, the analyzer 360 generates the position information, etc. of the DH region, which are described above, detected in the fundus image to be analyzed, using the position information of the coordinate system defined in the projection image. Here, the fundus image to be analyzed may be a fundus image in which the region, etc. corresponding to the optic disc has been corrected by the position matching with the projection image.

The analyzer 360 can generate statistical information on the position information of the DH region, the shape information of the DH region, and the occurrence information of the DH region. Examples of the statistical information include statistical information for eyes of a plurality of subjects, and statistical information for the same subject's eye (or same subject). Examples of statistical information include a histogram.

Further, the analyzer 360 can manage the position information of the DH region, the shape information of the DH region, and the occurrence information of the DH region, or the statistical information thereof, in chronological order, in association with the date of detection of the DH region or the date of occurrence of the DH region estimated by the doctor.

The position information generator 361 generates the position information that represents the position of the DH region or the direction of the DH region, etc. with reference to a reference position in the fundus image. For example, the reference position is identified by analyzing the fundus image or the projection image. Examples of the reference position include a center of the optic disc and a center of gravity of the optic disc.

In some embodiments, the position information includes information indicating a representative position of the detected DH region with reference to the center of the optic disc (information indicating a relative position of the DH region with reference to the center of the optic disc). Examples of the representative position of the DH region include a center position of the DH region, a position of the center of gravity of the DH region, a position in the DH region closest to the reference position, and a position in the DH region farthest from the reference position.

In some embodiments, the position information includes information indicating a direction of the representative position of the detected DH region with reference to the center of the optic disc (angle with reference to a reference direction passing the center of the optic disc).

In some embodiments, the position information includes information indicating whether the representative position of the detected DH region is within or outside the optic disc. In some embodiments, the position information includes information indicating whether the representative position of the detected DH region is within the neuroretinal rim (simply, rim) within the optic disc region or outside the neuroretinal rim within the optic disc region.

The position information generator 361 can generate at least one of the plurality of position information described above.

The shape information generator 362 generates the shape information representing the shape of the DH region detected in the fundus image. In this case, the shape information generator 362 can quantitatively generate the shape information of the DH region in the fundus image, using the shape of the DH region in the OCT coordinate system and the size information per pixel (pixel spacing) in the OCT coordinate system.

In some embodiments, the shape information includes information indicating at least one of an ellipticity of the DH region and an area of the DH region. For example, the ellipticity is obtained by performing elliptical approximation on the DH region and calculating the ratio of the minor axis to the major axis of the identified ellipse. For example, the area of the DH region is quantitatively obtained by identifying the boundaries of the DH region, counting the number of pixels within the identified boundaries, and using the size information per pixel in the OCT coordinate system.

The shape information generator 362 can generate at least one of the plurality of shape information described above.

The occurrence information generator 363 generates the occurrence information of the detected DH region. For example, the occurrence information generator 363 (analyzer 360) generates the occurrence information of the DH region based on the date of detection of the DH region that has occurred in the past for eyes of a plurality of subjects or the subject's eye to be analyzed, or the date of occurrence of the DH region estimated by the doctor.

In some embodiments, the occurrence information includes at least one of the occurrence frequency of the DH region and the occurrence interval of the DH region.

Examples of the occurrence frequency include an occurrence frequency of the DH region in the eyes of a plurality of subjects or the same subject's eye, and a frequency for each occurrence position of the DH region in the eyes of a plurality of subjects or the same subject's eye. Examples of the frequency for each occurrence position include a frequency for each block divided radially with reference to a reference position. In this case, the occurrence information is obtained for the occurrence position of the DH region based on the above position information or for each block divided radially with reference to the reference position, the block being identified based on the above position information.

The occurrence interval is obtained by the interval between the date of detection of the current DH region or the date of occurrence of the current DH region estimated by the doctor and the most recently recorded date in the past of detection of the DH region or the most recently recorded date in the past of occurrence of the DH region estimated by the doctor.

FIG. 10 schematically shows an example of the position information generated by the position information generator 361 according to the first embodiment. FIG. 10 represents a histogram of the positions of the DH region in the eyes of the plurality of subjects. In FIG. 10, the direction of T (temporal) is 0 degrees and the direction of N (nasal) is 180 degrees, centered on the optic disc.

As shown in FIG. 10, it can be grasped that the DH region tends to occur in the direction of T (temporal) with reference to the center of the optic disc. Although FIG. 10 represents a histogram of the positions of the DH region for the eyes of the plurality of subjects, the position information generator 361 may generate a histogram of the positions of the DH region for the same subject's eye as shown in FIG. 10.

FIG. 11 schematically shows an example of the shape information generated by the shape information generator 362 according to the first embodiment. FIG. 11 represents a histogram of the areas of the DH region in the eyes of a plurality of subjects. In FIG. 11, the vertical axis represents frequency and the horizontal axis represents area [mm$^2$].

As shown in FIG. 11, the distribution of the areas of the DH region can be grasped. Although FIG. 11 represents a histogram of the areas of the DH region for the eyes of the plurality of subjects, the shape information generator 362 may generate a histogram of the areas of the DH region for the same subject's eye shown in FIG. 11.

In some embodiments, the analyzer 360 performs position matching between the fundus image in which the DH region has been detected by the detector 320 and a layer thickness map of a predetermined layer region of the fundus Ef obtained by a known method by performing OCT measurement, and generates a composite image superimposing the fundus image and the layer thickness map. Examples of the predetermined layer region include ganglion cell layer (GCL), retinal nerve fiber layer (RNFL), circumpapillary retinal nerve fiber layer (cpRNFL), GCC (=NFL+GCL+IPL (inner plexiform layer)). In this case, the controller 210 (main controller 211) can display the generated composite image on the display unit 240A described below.

In some embodiments, the analyzer 360 estimates the time (or date) of the occurrence of the DH region based on a color of the DH region detected by the detector 320. For example, the analyzer 360 estimates the time of the occurrence of the DH region based on the color of the detected DH region with reference to a reference color of the DH region. The color of the DH region is mainly identified by extracting the red component in the fundus image. In some embodiments, the analyzer 360 estimates the interval of the occurrence of DH region based on a difference in color (e.g., pixel value of the red component) of the DH region detected last time and this time. In some embodiments, the analyzer 360 estimates the time of the occurrence of the DH region based on the color of the DH region detected on the previous inspection date and the interval of the occurrence of the DH region.

The data processor 300 that functions described above includes, for example, a processor described above, a RAM, a ROM, a hard disk drive, a circuit board, and the like. In a storage device such as the hard disk drive, a computer program for causing the processor to execute the functions described above is stored in advance.

(User Interface)

As shown in FIG. 3, the user interface 240 includes the display unit 240A and the operation unit 240B. The display unit 240A includes the display device of the arithmetic control unit 200 described above and/or the display apparatus 3. The operation unit 240B includes the operation device of the arithmetic control unit 200 described above. The operation unit 240B may include various kinds of buttons and keys provided on the housing of the ophthalmic apparatus 1, or provided outside the ophthalmic apparatus 1. For example, when the fundus camera unit 2 has a case similar to that of the conventional fundus camera, the operation unit 240B may include a joy stick, an operation panel, and the like provided to the case. Further, the display unit 240A may include various kinds of display devices, such as a touch panel placed on the housing of the fundus camera unit 2.

It should be noted that the display unit 240A and the operation unit 240B need not necessarily be formed as separate devices. For example, a device like a touch panel, which has a display function integrated with an operation function, can be used. In such cases, the operation unit 240B includes the touch panel and a computer program. The content of operation performed on the operation unit 240B is fed to the controller 210 as an electric signal. Moreover, operations and inputs of information may be performed using a graphical user interface (GUI) displayed on the display unit 240A and the operation unit 240B.

The data processor 300 is an example of the "ophthalmic information processing apparatus" according to the embodiments. The projection image is an example of the "OCT data" according to the embodiments. The fundus camera unit 2 (imaging optical system 30) is an example of the "imaging unit" according to the embodiments. The OCT unit 100 and the image forming unit 230 (and/or the data processor 300) are an example of the "OCT unit" according to the embodiments.

[Operation]

The operation of the ophthalmic apparatus 1 according to the first embodiment will be described.

Figure 12:
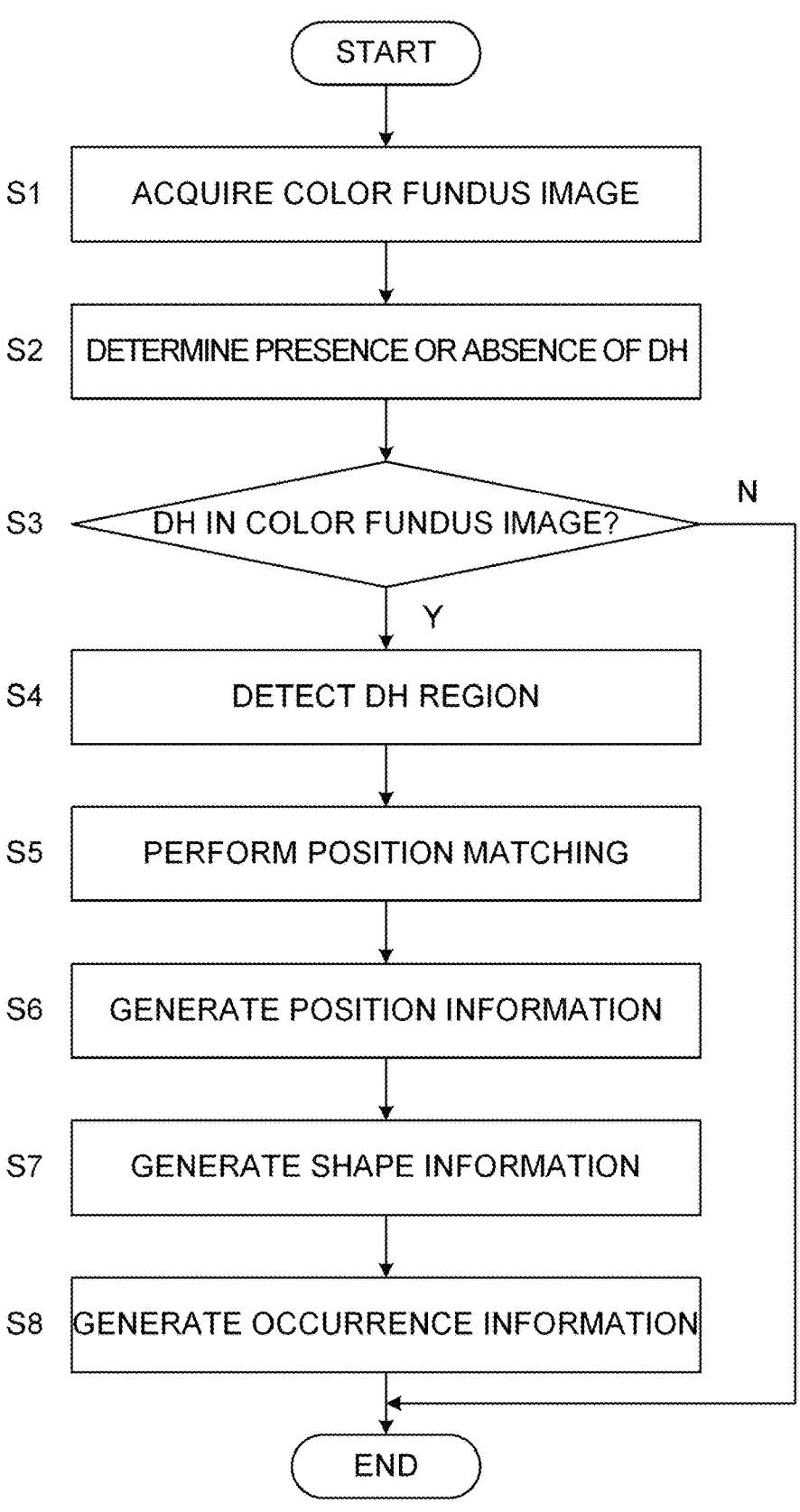
FIG. 12 is a flowchart illustrating an example of an operation of the ophthalmic apparatus according to the first embodiment.

FIG. 12 shows an operation example of the ophthalmic apparatus 1 according to the first embodiment. FIG. 12 shows a flowchart of an example of the operation of the ophthalmic apparatus 1 according to the first embodiment. The storage unit 212 stores computer programs for realizing the processing shown in FIG. 12. The main controller 211 operates according to the computer programs, and thereby the main controller 211 performs the processing shown in FIG. 12.

In the following, it is assumed that alignment between the subject's eye E and the optical system has already been completed. It is assumed that machine learning has already been performed on the DH determination model 311 by the first learning unit 410 and machine learning has already been performed on the DH region detection model 321 by the second learning unit 420.

(S1: Acquire Color Fundus Image)

First, the main controller 211 (controller 210) controls the fundus camera unit 2 (imaging optical system 30) to photograph the fundus Ef of the subject's eye E. Thereby, the main controller 211 can acquire the color fundus image of the subject's eye E.

(S2: Determine Presence or Absence of DH)

Next, the main controller 211 controls the determiner 310 to determine whether or not the color fundus image acquired in step S1 has the DH.

The determiner 310 determines (classifies) whether or not the color fundus image has the DH using the DH determination model 311, as described above.

(S3: DH in Color Fundus Image?)

When it is determined in step S2 that the color fundus image has the DH (S3: Y), the operation of the ophthalmic apparatus 1 proceeds to step S4.

When it is determined in step S2 that the color fundus image does not have the DH (S3: N), the ophthalmic apparatus 1 terminates the operation (END).

(S4: Detect DH Region)

When it is determined in step S2 that the color fundus image has the DH (S3: Y), the main controller 211 controls the detector 320 to detect the DH region in the color fundus image that is determined to have the DH in step S2.

The detector 320 detects the DH region in the color fundus image that is determined to have the DH in step S2, using the DH region detection model 321, as described above.

(S5: Perform Position Matching)

Subsequently, the main controller 211 controls the position matching unit 350 to perform position matching between the fundus image in which the DH region has been detected in step S4 and the projection image formed based on the OCT data obtained by performing OCT measurement on the subject's eye E.

In some embodiments, after the DH region is detected in the fundus image in step S4, the main controller 211 controls the OCT unit 100 to perform OCT measurement, controls the image forming unit 230 to form the OCT image, and controls the projection image forming unit 340 to form the projection image.

In some embodiments, OCT measurement is performed on the subject's eye in advance, and the projection image of the subject's eye E is formed by the projection image forming unit 340.

(S6: Generate Position Information)

Subsequently, the main controller 211 controls the position information generator 361 to generate the position information of the DH region in the fundus image on which the position matching has been performed in step S5.

For example, the position information generator 361 obtains the relative position of the representative position of the DH region to the center of the optic disc. For example, the position information generator 361 obtains the direction of the representative position of the DH region with reference to the center of the optic disc and generates the position information as shown in FIG. 10.

(S7: Generate Shape Information)

Subsequently, the main controller 211 controls the shape information generator 362 to generate the shape information of the DH region in the fundus image on which the position matching has been performed in step S5.

For example, the shape information generator 362 obtains the area of the DH region, and generates the shape information as shown in FIG. 11, as described above.

(S8: Generate Occurrence Information)

Subsequently, the main controller 211 controls the occurrence information generator 363 to generate the occurrence information of the DH region detected in step S4.

For example, the occurrence information generator 363 generates the occurrence information including the occurrence frequency of the DH region and the occurrence interval of the DH region, as described above.

This terminates the operation of the ophthalmic apparatus 1.

Here, the detection accuracy of the DH region by the ophthalmic apparatus 1 according to the first embodiment will be explained.

Figure 13:
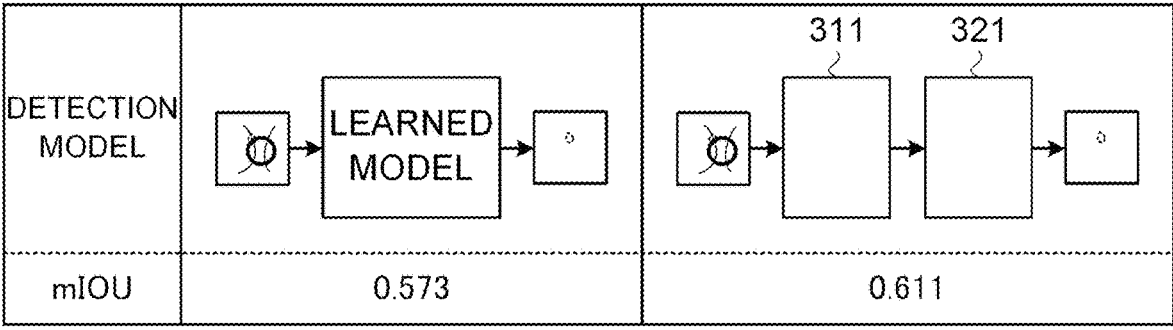
FIG. 13 is a schematic diagram for explaining an operation of the ophthalmic apparatus according to the first embodiment.

FIG. 13 shows a diagram for explaining the detection accuracy of the DH region by the ophthalmic apparatus 1 according to the first embodiment. FIG. 13 schematically represents the detection accuracy of the DH region by the ophthalmic apparatus 1 according to the first embodiment by contrasting it with a comparative example of the first embodiment. In the comparative example of the first embodiment, a single learned model (ResUnet++) is generated by performing machine learning, and the DH region is detected directly from the fundus image using the generated learned model.

In FIG. 13, mIOU (mean Intersection Over Union) is used as an index of the detection accuracy of the DH region. The mIOU corresponds to the average of the IOUs calculated for each image. Here, IOU represents a ratio of the number of pixels in the true positive region (TP) to the sum of the number of pixels in the positive region (P) and the number of pixels in the true region (T) in the fundus image as the input image and the detection image (DH region detection image) as the output image, as represented in Equation (1). In other words, IOU is the index indicating that the closer to "1", the higher the detection accuracy.

[Equation 1]

$$IOU = \frac{TP}{P + T - TP} \quad (1)$$

In the present embodiment, the positive region corresponds to the region detected to be the DH region in the detection image (output image). The true region corresponds to the true DH region in the fundus image. The true positive region corresponds to the region (the correct region) where the DH region detected in the detection image matches the true DH region in the fundus image.

FIG. 13 represents mIOU (average of 146×2 IOUs) by the configuration for the comparison example and mIOU by the configuration according to the first embodiment, for 146 images with DH and 146 images without DH. That is, in the comparative example, in the case where the DH region is detected using a single learned model as described above, the mIOU=0.573. In contrast, in the case where the DH region is detected using the DH determination model 311 and the DH region detection model 321 in the first embodiment, the mIOU=0.611.

Therefore, FIG. 13 represents that the DH region can be detected with high accuracy according to the configuration of the first embodiment compared to the comparison example.

As described above, according to the first embodiment, the DH region can be detected with higher precision and higher reproducibility, compared to when the DH region in the fundus image is detected using a single learned model.

In addition, since the position matching is performed between the fundus image in which the DH region has been detected and the projection image and the position information, the shape information, and the occurrence information of the DH region are generated using the OCT data, the detected DH region can be evaluated quantitatively with high accuracy.

Second Embodiment

In the first embodiment, the case where the DH region in the fundus image is detected by the ophthalmic apparatus to which the ophthalmic information processing apparatus according to the embodiments has been described. However, the configuration according to the embodiments is not limited to this.

In the second embodiment, the ophthalmic information processing apparatus according to the embodiments can perform detection processing of the DH region described above on the fundus image or the OCT data (projection image) that are acquired using one or more external apparatuses. In the following, the second embodiment will be described with a focus on differences from the first embodiment.

Figure 14:
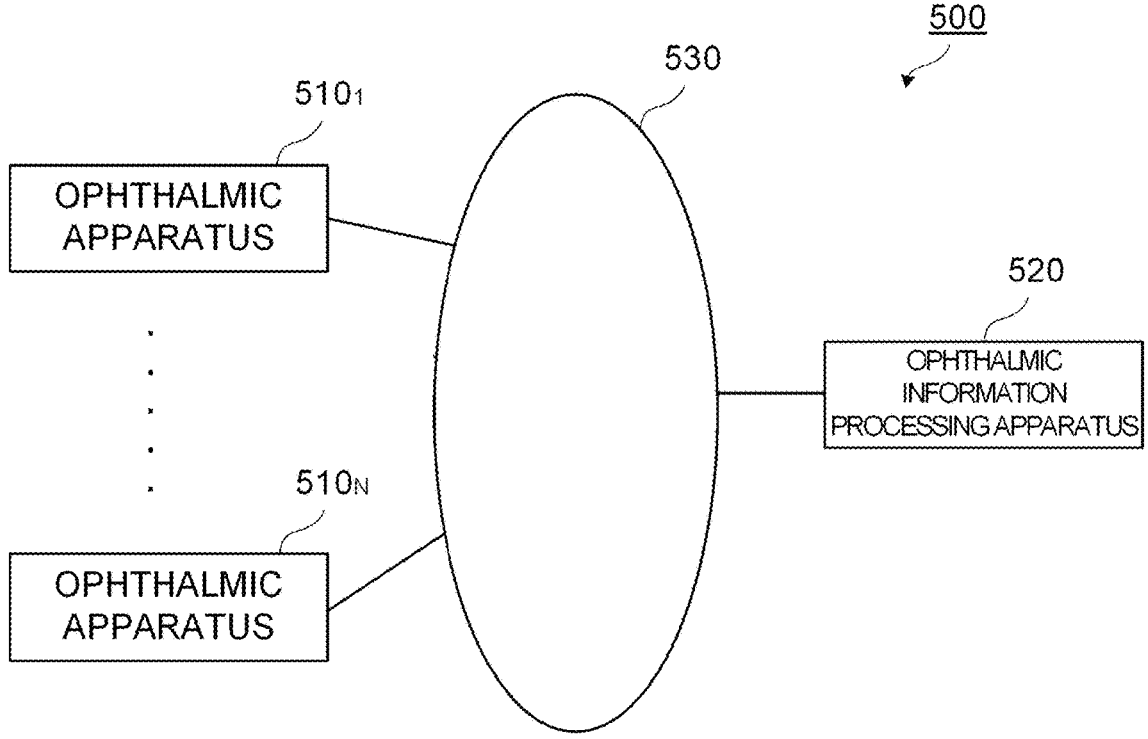
FIG. 14 is a schematic diagram illustrating a first configuration example of an ophthalmic system according to a second embodiment.

FIG. 14 shows a block diagram of a first configuration example of an ophthalmic system according to the second embodiment.

The ophthalmic system 500 according to the first configuration example includes ophthalmic apparatuses 510₁ to 510_N (N is an integer of 2 or more) and an ophthalmic information processing apparatus 520. The ophthalmic information processing apparatus 520 is connected to the ophthalmic apparatuses 510₁ to 510_N via a network 530. The network 530 may be a wired or wireless network (LAN, WAN).

The ophthalmic information processing apparatus 520 can communicate with any of the ophthalmic apparatuses 510₁ to 510_N.

In some embodiments, any of the ophthalmic apparatuses 510₁ to 510_N transmits a request to the ophthalmic information processing apparatus 520, and the ophthalmic apparatus whose request is approved transmits data to the ophthalmic information processing apparatus 520. The transmitted data includes the image data of the fundus image of the subject's eye E and the OCT data or the image data of the projection image of subject's eye E described above.

In some embodiments, the ophthalmic information processing apparatus 520 transmits a request to any of the ophthalmic apparatuses 510₁ to 510_N and receives data from the ophthalmic apparatus that approved the request. The received data includes the image data of the fundus image of the subject's eye E and the OCT data or the image data of the projection image of the subject's eye E described above.

Figure 15:
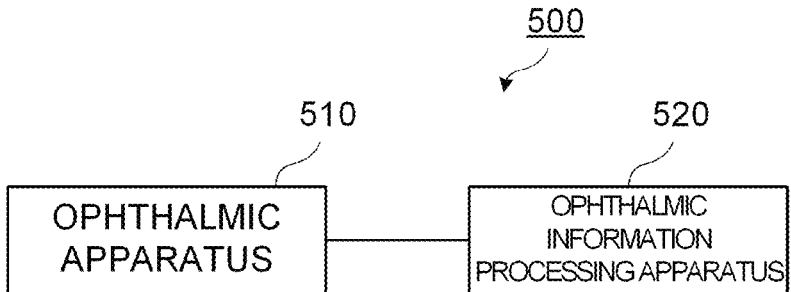
FIG. 15 is a schematic diagram illustrating a second configuration example of the ophthalmic system according to the second embodiment.

FIG. 15 shows a block diagram of a second configuration example of the ophthalmic system according to the second embodiment.

The ophthalmic system 500 according to the second configuration example includes an ophthalmic apparatus 510 and the ophthalmic information processing apparatus 520. The ophthalmic information processing apparatus 520 is connected to the ophthalmic apparatus 510 via a predetermined communication path. In some embodiments, the ophthalmic information processing apparatus 520 is peer-to-peer connected to the ophthalmic apparatus 510 via a network.

The ophthalmic information processing apparatus 520 can communicate with the ophthalmic apparatus 510.

In some embodiments, the ophthalmic apparatus 510 transmits a request to the ophthalmic information processing apparatus 520, and the ophthalmic apparatus 510 whose request is approved transmits data to the ophthalmic information processing apparatus 520. The transmitted data includes the image data of the fundus image of the subject's eye E and the OCT data or the image data of the projection image of subject's eye E described above.

In some embodiments, the ophthalmic information processing apparatus 520 transmits a request to the ophthalmic apparatus 510, and receives data from the ophthalmic apparatus 510 that approves the request. The received data includes the image data of the fundus image of the subject's eye E and the OCT data or the image data of the projection image of the subject's eye E described above.

The ophthalmic apparatuses 510₁ to 510ₙ and the ophthalmic apparatus 510 have substantially the same configurations as the ophthalmic apparatus 1 shown in FIGS. 1 to 3. In the second embodiment, a part of the functions of the data processor 300 among the functions of the ophthalmic apparatus 1 shown in FIGS. 1 to 3 is realized by the ophthalmic information processing apparatus 520.

Figure 16:
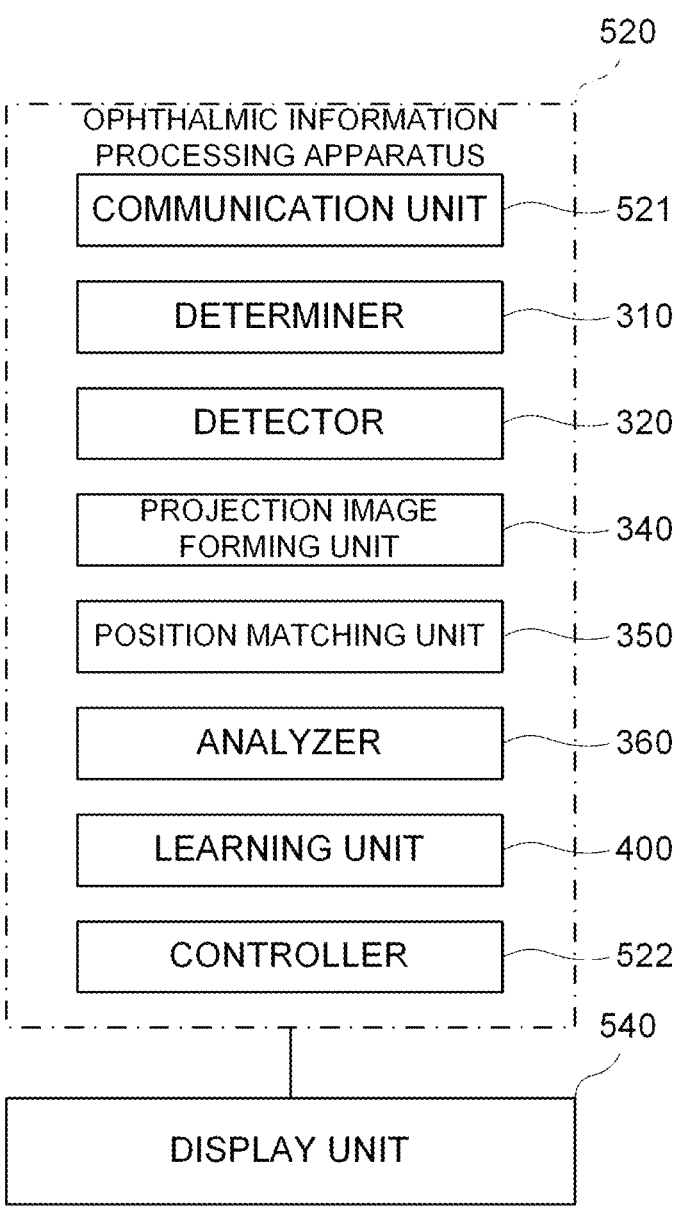
FIG. 16 is a schematic diagram illustrating an example of a configuration of an ophthalmic information processing apparatus according to the second embodiment.

FIG. 16 shows a block diagram of an example of the configuration of the ophthalmic information processing apparatus 520 according to the second embodiment. In FIG. 16, parts similar to those in FIG. 4 are denoted by the same reference symbols, and description thereof is omitted as appropriate.

The ophthalmic information processing apparatus 520 includes a communication unit 521, the determiner 310, the detector 320, the projection image forming unit 340, the position matching unit 350, the analyzer 360, the learning unit 400, and a controller 522. The learning unit 400 may not be includes in the ophthalmic information processing apparatus 520.

The communication unit 521 performs communication interface processing with the ophthalmic apparatus 510₁ to 510ₙ or the ophthalmic apparatus 510. That is, the communication unit 521 communicates with the ophthalmic apparatuses 510₁ to 510ₙ or the ophthalmic apparatus 510 according to a predetermined communication protocol, and receives the communication data including the image data of the fundus image from the ophthalmic apparatuses 510₁ to 510ₙ or the ophthalmic apparatus 510 and the OCT data or the image data of the projection image of the subject's eye E described above. The communication unit 521 acquires the fundus and the OCT data of the subject's eye acquired by the ophthalmic apparatus, by receiving the image data included in the received communication data.

The controller 522 includes a processor and controls each part of the ophthalmic information processing apparatus 520, in the same manner as the controller 210. The controller 522 includes a main controller and a storage unit, in the same manner as the controller 210.

Further, the controller 522 can perform display control on a display unit 540 connected to the outside of the ophthalmic information processing apparatus 520, as a display controller. The display unit 540 has the same function as the display unit 240A.

The operation of the ophthalmic information processing apparatus 520 is similar to the flow shown in FIG. 12, except that the fundus image and the projection image (OCT data) are acquired from an external device, so a detailed description will be omitted. In other words, the ophthalmic information processing apparatus 520 determines the presence or absence of the DH in fundus images acquired from the ophthalmic apparatuses 510₁ to 510ₙ, as in the first embodiment, and detects the DH region in the fundus image determined to have the DH. Furthermore, the ophthalmic information processing apparatus 520 performs position matching with the fundus image using the OCT data acquired from the ophthalmic apparatuses 510₁ to 510ₙ or the ophthalmic apparatus 510, and obtains the analysis result(s) such as the positional information of the DH region described above.

The configuration of the ophthalmic system 500 according to the second embodiment is not limited to the configurations shown in FIGS. 14 and 15.

Figure 17:
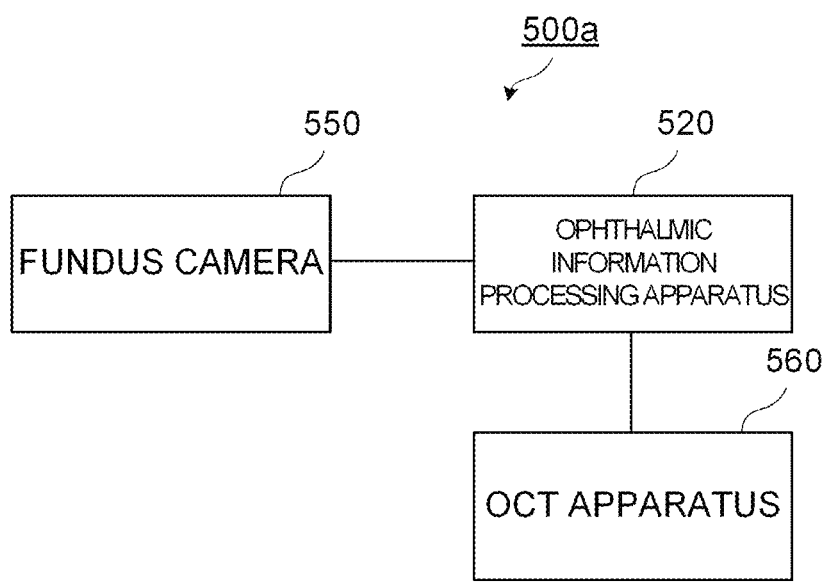
FIG. 17 is a schematic diagram illustrating an example of a configuration of an ophthalmic system according to a first modification example of the second embodiment.

FIG. 17 shows an example of a configuration of an ophthalmic system according to a first modification example of the second embodiment.

The ophthalmic system 500a according to the first modification example of the second embodiment includes an ophthalmic information processing apparatus 520, a fundus camera 550, and an OCT apparatus 560. The ophthalmic information processing apparatus 520 can communicate with each of the fundus camera 550 and the OCT apparatus 560.

The fundus camera 550 has the function of the fundus camera unit 2 of the ophthalmic apparatus 1 according to the first embodiment (i.e., the function of acquiring fundus images). The OCT apparatus 560 has some of the functions of the OCT unit 100, the image forming unit 230, and the data processor 300 of the ophthalmic apparatus 1 according to the first embodiment (i.e., the functions of acquiring OCT data and forming OCT images).

The ophthalmic information processing apparatus 520 acquires the image data of the fundus image(s) of the subject's eye E from the fundus camera 550, and acquires the OCT data (or the image data of the projection image(s)) of the subject's eye E from the OCT apparatus 560. The ophthalmic information processing apparatus 520 determines the presence or absence of the DH in fundus image acquired from the fundus camera 550, as in the first embodiment, and detects the DH region in the fundus image determined to have the DH. Furthermore, the ophthalmic information processing apparatus 520 performs position matching with the fundus image using the OCT data acquired from the OCT apparatus 560, and obtains the analysis result(s) such as the positional information of the DH region described above.

Figure 18:
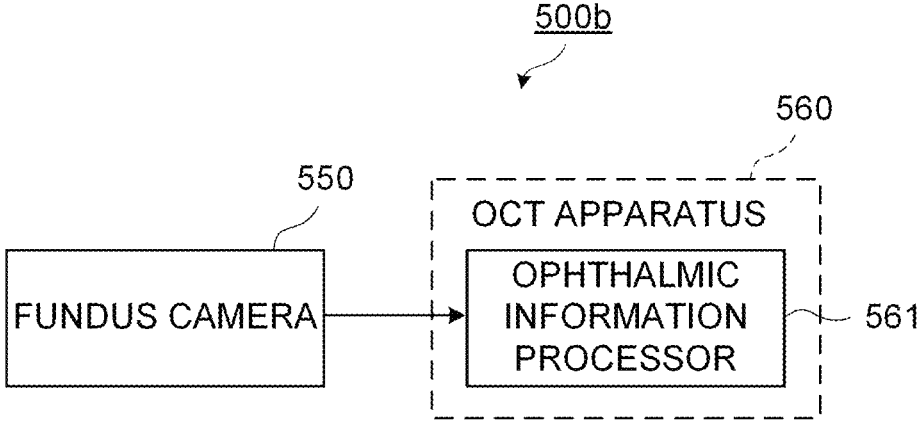
FIG. 18 is a schematic diagram illustrating an example of a configuration of an ophthalmic system according a second modification example of the second embodiment.

FIG. 18 shows an example of a configuration of an ophthalmic system according to a second modification example of the second embodiment.

The ophthalmic system 500b according to the second modification example of the second embodiment includes the fundus camera 550 and the OCT apparatus 560. The OCT apparatus 560 includes an ophthalmic information processor 561. The OCT apparatus 560 can communicate with the fundus camera 550.

The fundus camera 550 has the function of the fundus camera unit 2 of the ophthalmic apparatus 1 according to the first embodiment (i.e., the function of acquiring fundus images). The OCT apparatus 560 has some of the functions of the OCT unit 100, the image forming unit 230, and the data processor 300 of the ophthalmic apparatus 1 according to the first embodiment (i.e., the functions of acquiring OCT data and forming OCT images). The ophthalmic information processor 561 has the function of the ophthalmic information processing apparatus 520.

The ophthalmic information processor 561 acquires the image data of the fundus image(s) of the subject's eye E from the fundus camera 550, and performs analysis processing performed by the analyzer 360 described above using the OCT data (or the image data of the projection image(s)) of the subject's eye E acquired in the OCT apparatus 560. The ophthalmic information processor 561 determines the presence or absence of the DH in fundus image acquired from the fundus camera 550, as in the first embodiment, and detects the DH region in the fundus image determined to have the DH. Furthermore, the ophthalmic information processor 561 performs position matching with the fundus image using the OCT data acquired in the OCT apparatus 560, and obtains the analysis result(s) such as the positional information of the DH region described above.

[Actions]

The ophthalmic information processing apparatus, the ophthalmic apparatus, the ophthalmic information processing method, and the program according to the embodiments will be described.

An ophthalmic information processing apparatus (data processor 300, ophthalmic information processing apparatus 520, ophthalmic information processor 561) includes a determiner (310) and a detector (320). The determiner is configured to determine a presence or absence of a disc hemorrhage for a front image (fundus image IMG0) of a fundus (Ef) of a subject's eye (E), using a disc hemorrhage determination model (311) obtained by performing machine learning using a plurality of fundus images (LIMG) labeled with labels indicating the presence or absence of a disc hemorrhage as first teaching data. The detector is configured to detect a disc hemorrhage region depicted in the front image that is determined to have the disc hemorrhage, using a disc hemorrhage region detection model (322) obtained by performing machine learning using a plurality of pairs of image groups as second teaching data, each pair having a front image (IMG1) of a fundus and a disc hemorrhage region image (TG1) representing a disc hemorrhage region depicted in the front image.

According to such an aspect, the presence or absence of the disc hemorrhage is determined for the front image of the fundus of the subject's eye by the determiner, and the disc hemorrhage region in the front image is detected by the detector for the front image determined to have the disc hemorrhage. In this case, in the disc hemorrhage region detection model in the detector, the learning parameters are updated specifically for detection of the disc hemorrhage region, by performing machine learning using the fundus images alone in which the disc hemorrhage region exists. As a result, the accuracy of detection of the disc hemorrhage region can be improved. Therefore, the disc hemorrhage regions in the fundus images can be detected with higher reproducibility and accuracy, compared to detecting the disc hemorrhage region in the fundus image of the subject's eye using a single learned model.

In the ophthalmic information processing apparatus according to the embodiments, the second teaching data includes a front image included in the first teaching data.

According to such an aspect, machine learning is performed on each of the disc hemorrhage determination model of the determiner and the disc hemorrhage region detection model of the detector, using the same front image. Thereby, the disc hemorrhage region in the fundus image can be detected with high accuracy and higher reproducibility, without increasing the amount of teaching data.

The ophthalmic information processing apparatus according to the embodiments further includes a first learning unit (410) configured to generate the disc hemorrhage determination model by performing supervised machine learning using the first teaching data.

According to such an aspect, the disc hemorrhage determination model is learned by the first learning unit. Thereby, the ophthalmic information processing apparatus capable of improving the determination accuracy of the presence or absence of the disc hemorrhage can be provided.

The ophthalmic information processing apparatus according to the embodiments further includes a second learning unit (420) configured to generate the disc hemorrhage region detection model by performing supervised machine learning using the second teaching data.

According to such an aspect, the disc hemorrhage region detection model is learned by the second learning unit. Thereby, the ophthalmic information processing apparatus capable of improving the detection accuracy of the disc hemorrhage region can be provided.

In the ophthalmic information processing apparatus according to embodiments, the front image of the fundus is a color front image.

According to such an aspect, the determination accuracy by the determiner and the detection accuracy by the detector can be further improved using the front image with a larger amount of information.

The ophthalmic information processing apparatus further includes an analyzer (360) configured to generate at least one of position information of a position of the disc hemorrhage region in the front image of the fundus of the subject's eye, shape information representing a shape of the disc hemorrhage region, or occurrence information representing occurrence status of the disc hemorrhage region, by analyzing the front image of the fundus of the subject's eye.

According to such an aspect, the disc hemorrhage region detected with higher reproducibility and high accuracy is analyzed. Thereby, the analysis result of the disc hemorrhage region in the fundus image of the subject's eye can be obtained with higher reproducibility and high accuracy.

In the ophthalmic information processing apparatus according to the embodiments, the position information includes information indicating a direction of a representative position of the disc hemorrhage region relative to a reference position.

According to such an aspect, the direction of the occurrence position of the direction of the disc hemorrhage region with reference to the reference position in the fundus can be grasped easily. This allows to contribute to identify a future disease symptoms that are estimated according to the direction of occurrence of the disc hemorrhage region relative to the reference position and to determine a future treatment strategies.

In the ophthalmic information processing apparatus according to the embodiments, the position information includes information indicating whether the representative position of the disc hemorrhage region is within or outside an optic disc region.

According to such an aspect, it becomes easier to determine whether the disc hemorrhage region is within or outside the optic disc region. This allows to contribute to identify a future disease symptoms that are estimated depending on whether or not the disc hemorrhage region is within the optic disc region and to determine a future treatment strategies.

In the ophthalmic information processing apparatus according to the embodiments, the position information includes information indicating whether the representative position is within or outside a neuroretinal rim.

According to such an aspect, it becomes easier to determine whether the disc hemorrhage region is within or outside the neuroretinal rim. This allows to contribute to identify a future disease symptoms that are estimated depending on whether or not the disc hemorrhage region is within the neuroretinal rim and to determine a future treatment strategies.

In the ophthalmic information processing apparatus according to the embodiments, the shape information includes at least one of an ellipticity of the disc hemorrhage region or an area of the disc hemorrhage region.

According to such an aspect, the shape and the size of the disc hemorrhage region can be grasped easily. This allows to contribute to identify a future disease symptoms that are estimated according to the shape or the size of the disc hemorrhage region and to determine a future treatment strategies.

In the ophthalmic information processing apparatus according to the embodiments, the occurrence information includes at least one of an occurrence frequency of the disc hemorrhage region or an occurrence interval of the disc hemorrhage region.

According to such an aspect, the occurrence status of the disc hemorrhage region can be grasped easily. This allows to contribute to identify a future disease symptoms that are estimated according to the occurrence status of the disc hemorrhage region and to determine a future treatment strategies.

The ophthalmic information processing apparatus according to the embodiment further includes a position matching unit (350) configured to perform position matching between OCT data of the subject's eye and the front image of the subject's eye in which the disc hemorrhage region detected by the detector is depicted. The analyzer is configured to generate at least one of the position information, the shape information, or the occurrence information, using the OCT data on which position matching has been performed with the front image by the position matching unit.

According to such an aspect, the disc hemorrhage region in the fundus image is performed position matching with the OCT data. Thereby, the disc hemorrhage region can be identified in the OCT coordinate system that defines the OCT data acquired with high reproducibility and high accuracy. This allows to quantitatively obtain the analysis result (s) of the disc hemorrhage region with high reproducibility and high accuracy.

An ophthalmic apparatus (1) according to the embodiments includes an imaging unit (imaging optical system 30) configured to image the fundus of the subject's eye, and the ophthalmic information processing apparatus described above.

According to such an aspect, the ophthalmic apparatus capable of acquiring the front image of the subject's eye and detecting the disc hemorrhage region in the acquired front image with high reproducibility and with accuracy can be provided.

An ophthalmic apparatus (1) according to the embodiments includes an imaging unit (imaging optical system 30) configured to image the fundus of the subject's eye, an OCT unit (a part of OCT unit 100, image forming unit 230, and data processor 300) configured to acquire the OCT data by performing optical coherence tomography on the subject's eye, and the ophthalmic information processing apparatus described above.

According to such an aspect, the ophthalmic apparatus capable of acquiring the front image and the OCT data of the subject's eye and detecting the disc hemorrhage region in the acquired front image with high reproducibility and with accuracy can be provided. In addition, the analysis result(s)

of the disc hemorrhage region can be quantitatively obtained with high reproducibility and high accuracy.

An ophthalmic information processing method according to the embodiments includes a determination step and a detection step. The determination step is performed to determine a presence or absence of a disc hemorrhage for a front image of a fundus (Ef) of a subject's eye (E), using a disc hemorrhage determination model (311) obtained by performing machine learning using a plurality of fundus images (LIMG) labeled with labels indicating the presence or absence of a disc hemorrhage as first teaching data. The detection step is performed to detect a disc hemorrhage region depicted in the front image that is determined to have the disc hemorrhage in the determination step, using a disc hemorrhage region detection model (322) obtained by performing machine learning using a plurality of pairs of image groups as second teaching data, each pair having a front image (IMG1) of a fundus and a disc hemorrhage region image (TG1) representing a disc hemorrhage region depicted in the front image.

According to such an aspect, the presence or absence of the disc hemorrhage is determined for the front image of the fundus of the subject's eye in the determination step, and the disc hemorrhage region in the front image is detected in the detection step for the front image determined to have the disc hemorrhage. In this case, in the disc hemorrhage region detection model in the detection step, the learning parameters are updated specifically for detection of the disc hemorrhage region, by performing machine learning using the fundus images alone in which the disc hemorrhage region exists. As a result, the accuracy of detection of the disc hemorrhage region can be improved. Therefore, the disc hemorrhage regions in the fundus images can be detected with higher reproducibility and accuracy, compared to detecting the disc hemorrhage region in the fundus image of the subject's eye using a single learned model.

In the ophthalmic information processing method according to the embodiments, the second teaching data includes a front image included in the first teaching data.

According to such an aspect, machine learning is performed on each of the disc hemorrhage determination model in the determination step and the disc hemorrhage region detection model in the detection step, using the same front image. Thereby, the disc hemorrhage region in the fundus image can be detected with high accuracy and higher reproducibility, without increasing the amount of teaching data.

The ophthalmic information processing method according to the embodiments further includes a first learning step of generating the disc hemorrhage determination model by performing supervised machine learning using the first teaching data.

According to such an aspect, the disc hemorrhage determination model is learned in the first learning step. Thereby, the ophthalmic information processing method capable of improving the determination accuracy of the presence or absence of the disc hemorrhage can be provided.

The ophthalmic information processing method according to the embodiments further includes a second learning step of generating the disc hemorrhage region detection model by performing supervised machine learning using the second teaching data.

According to such an aspect, the disc hemorrhage region detection model is learned in the second learning step. Thereby, the ophthalmic information processing method capable of improving the detection accuracy of the disc hemorrhage region can be provided.

In the ophthalmic information processing method of the embodiments, the front image of the fundus is a color front image.

According to such an aspect, the determination accuracy in the determination step and the detection accuracy in the detection step can be further improved using the front image with a larger amount of information.

The ophthalmic information processing method according to the embodiments further includes an analyzing step of generating at least one of position information of a position of the disc hemorrhage region in a front image of the fundus of the subject's eye, shape information representing a shape of the disc hemorrhage region, or occurrence information representing occurrence status of the disc hemorrhage region, by analyzing the front image of the fundus of the subject's eye.

According to such an aspect, the disc hemorrhage region detected with higher reproducibility and high accuracy is analyzed. Thereby, the analysis result of the disc hemorrhage region in the fundus image of the subject's eye can be obtained with higher reproducibility and high accuracy.

In the ophthalmic information processing method according to the embodiments, the position information includes information indicating a direction of a representative position of the disc hemorrhage region relative to a reference position.

According to such an aspect, the direction of the occurrence position of the direction of the disc hemorrhage region with reference to the reference position in the fundus can be grasped easily. This allows to contribute to identify a future disease symptoms that are estimated according to the direction of occurrence of the disc hemorrhage region relative to the reference position and to determine a future treatment strategies.

In the ophthalmic information processing method according to the embodiments, the position information includes information indicating whether the representative position of the disc hemorrhage region is within or outside an optic disc region.

According to such an aspect, it becomes easier to determine whether the disc hemorrhage region is within or outside the optic disc region. This allows to contribute to identify a future disease symptoms that are estimated depending on whether or not the disc hemorrhage region is within the optic disc region and to determine a future treatment strategies.

In the ophthalmic information processing method according to the embodiments, the position information includes information indicating whether the representative position is within or outside a neuroretinal rim.

According to such an aspect, it becomes easier to determine whether the disc hemorrhage region is within or outside the neuroretinal rim. This allows to contribute to identify a future disease symptoms that are estimated depending on whether or not the disc hemorrhage region is within the neuroretinal rim and to determine a future treatment strategies.

In the ophthalmic information processing method according to the embodiments, the shape information includes at least one of an ellipticity of the disc hemorrhage region or an area of the disc hemorrhage region.

According to such an aspect, the shape and the size of the disc hemorrhage region can be grasped easily. This allows to contribute to identify a future disease symptoms that are estimated according to the shape or the size of the disc hemorrhage region and to determine a future treatment strategies.

In the ophthalmic information processing method according to the embodiments, the occurrence information includes at least one of an occurrence frequency of the disc hemorrhage region or an occurrence interval of the disc hemorrhage region.

According to such an aspect, the occurrence status of the disc hemorrhage region can be grasped easily. This allows to contribute to identify a future disease symptoms that are estimated according to the occurrence status of the disc hemorrhage region and to determine a future treatment strategies.

The ophthalmic information processing method according to the embodiments further includes a position matching step of performing position matching between OCT data of the subject's eye and the front image of the subject's eye in which the disc hemorrhage region detected in the detection step. The analyzing step is performed to generate at least one of the position information, the shape information, or the occurrence information, using the OCT data on which position matching has been performed with the front image in the position matching step.

According to such an aspect, the disc hemorrhage region in the fundus image is performed position matching with the OCT data. Thereby, the disc hemorrhage region can be identified in the OCT coordinate system that defines the OCT data acquired with high reproducibility and high accuracy. This allows to quantitatively obtain the analysis result (s) of the disc hemorrhage region with high reproducibility and high accuracy.

A program according to the embodiments causes a computer to execute each step of the ophthalmic information processing method of any one of described above.

According to such an aspect, the presence or absence of the disc hemorrhage is determined for the front image of the fundus of the subject's eye in the determination step, and the disc hemorrhage region in the front image is detected in the detection step for the front image determined to have the disc hemorrhage. In this case, in the disc hemorrhage region detection model in the detection step, the learning parameters are updated specifically for detection of the disc hemorrhage region, by performing machine learning using the fundus images alone in which the disc hemorrhage region exists. As a result, the accuracy of detection of the disc hemorrhage region can be improved. Therefore, the disc hemorrhage regions in the fundus images can be detected with higher reproducibility and accuracy, compared to detecting the disc hemorrhage region in the fundus image of the subject's eye using a single learned model.

<Others>

The above-described embodiments are merely examples for carrying out the present invention. Those who intend to implement the present invention can apply any modification, omission, addition, or the like within the scope of the gist of the present invention.

In some embodiments, a program for causing a computer to execute the method of controlling the ophthalmic apparatus described above is provided. Such a program can be stored in any non-transitory recording medium that can be read by a computer. Examples of the recording medium include a semiconductor memory, an optical disk, a magneto-optical disk (CD-ROM, DVD-RAM, DVD-ROM, MO, etc.), a magnetic storage medium (hard disk, floppy (registered trade mark) disk, ZIP, etc.), and the like. The computer program may be transmitted and received through a network such as the Internet, LAN, etc.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in Superguide v. DIRECTV, 69 USPQ2d 1865 (Fed. Cir. 2004).

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmic information processing apparatus, comprising:

a determiner circuit configured to determine a presence or absence of a disc hemorrhage for a front image of a fundus of a subject's eye, using a disc hemorrhage determination model obtained by performing machine learning using a plurality of fundus images labeled with labels indicating the presence or absence of a disc hemorrhage as first teaching data;

a detector circuit configured to detect a disc hemorrhage region depicted in the front image that is determined to have the disc hemorrhage by the determiner, using a disc hemorrhage region detection model obtained by performing machine learning using a plurality of pairs of image groups as second teaching data, each pair having a front image of a fundus and a disc hemorrhage region image representing a disc hemorrhage region depicted in the front image; and an analyzer circuit configured to generate at least one of position information of a position of the disc hemorrhage region in the front image of the fundus of the subject's eye, shape information representing a shape of the disc hemorrhage region, or occurrence information representing occurrence status of the disc hemorrhage region, by analyzing the front image of the fundus of the subject's eye.

2. The ophthalmic information processing apparatus of claim 1, wherein the second teaching data includes a front image included in the first teaching data.

3. The ophthalmic information processing apparatus of claim 1, further comprising a first learning circuit configured to generate the disc hemorrhage determination model by performing supervised machine learning using the first teaching data.

4. The ophthalmic information processing apparatus of claim 1, further comprising a second learning circuit configured to generate the disc hemorrhage region detection model by performing supervised machine learning using the second teaching data.

5. The ophthalmic information processing apparatus of claim 1, wherein the front image of the fundus is a color front image.

6. The ophthalmic information processing apparatus of claim 1, wherein the position information includes information indicating a direction of a representative position of the disc hemorrhage region relative to a reference position.

7. The ophthalmic information processing apparatus of claim 1, wherein the position information includes information indicating whether the representative position of the disc hemorrhage region is within or outside an optic disc region.

8. The ophthalmic information processing apparatus of claim 7, wherein the position information includes information indicating whether the representative position is within or outside a neuroretinal rim.

9. The ophthalmic information processing apparatus of claim 1, wherein the shape information includes at least one of an ellipticity of the disc hemorrhage region or an area of the disc hemorrhage region.

10. The ophthalmic information processing apparatus of claim 1, wherein the occurrence information includes at least one of an occurrence frequency of the disc hemorrhage region or an occurrence interval of the disc hemorrhage region.

11. The ophthalmic information processing apparatus of claim 1, further comprising a position matching circuit configured to perform position matching between OCT data of the subject's eye and the front image of the subject's eye in which the disc hemorrhage region detected by the detector is depicted, wherein the analyzer circuit is configured to generate at least one of the position information, the shape information, or the occurrence information, using the OCT data on which position matching has been performed with the front image by the position matching circuit.

12. An ophthalmic apparatus, comprising:

an imaging unit including a camera and configured to image the fundus of the subject's eye;

an OCT device including a scanner and configured to acquire the OCT data by performing optical coherence tomography on the subject's eye; and the ophthalmic information processing apparatus of claim 11.

13. An ophthalmic apparatus, comprising:

an imaging unit including a camera and configured to image the fundus of the subject's eye; and the ophthalmic information processing apparatus of claim 1.

14. An ophthalmic information processing method, comprising:

a determination step of determining a presence or absence of a disc hemorrhage for a front image of a fundus of a subject's eye, using a disc hemorrhage determination model obtained by performing machine learning using a plurality of fundus images labeled with labels indicating the presence or absence of a disc hemorrhage as first teaching data;

a detection step of detecting a disc hemorrhage region depicted in the front image that is determined to have the disc hemorrhage in the determination step, using a disc hemorrhage region detection model obtained by performing machine learning using a plurality of pairs of image groups as second teaching data, each pair having a front image of a fundus and a disc hemorrhage region image representing a disc hemorrhage region depicted in the front image; and an analyzing step of generating at least one of position information of a position of the disc hemorrhage region in a front image of the fundus of the subject's eye, shape information representing a shape of the disc hemorrhage region, or occurrence information representing occurrence status of the disc hemorrhage region, by analyzing the front image of the fundus of the subject's eye.

15. The ophthalmic information processing method of claim 14, wherein
the second teaching data includes a front image included in the first teaching data.

16. The ophthalmic information processing method of claim 14, further comprising
a first learning step of generating the disc hemorrhage determination model by performing supervised machine learning using the first teaching data.

17. The ophthalmic information processing method of claim 14, further comprising
a second learning step of generating the disc hemorrhage region detection model by performing supervised machine learning using the second teaching data.

18. The ophthalmic information processing method of claim 14, wherein
the front image of the fundus is a color front image.

19. The ophthalmic information processing method of claim 14, wherein
the position information includes information indicating a direction of a representative position of the disc hemorrhage region relative to a reference position.

20. The ophthalmic information processing method of claim 14, wherein the position information includes information indicating whether the representative position of the disc hemorrhage region is within or outside an optic disc region.

21. The ophthalmic information processing method of claim 20, wherein
the position information includes information indicating whether the representative position is within or outside a neuroretinal rim.

22. The ophthalmic information processing method of claim 14, wherein
the shape information includes at least one of an ellipticity of the disc hemorrhage region or an area of the disc hemorrhage region.

23. The ophthalmic information processing method of claim 14, wherein
the occurrence information includes at least one of an occurrence frequency of the disc hemorrhage region or an occurrence interval of the disc hemorrhage region.

24. The ophthalmic information processing method of claim 14, further comprising
a position matching step of performing position matching between OCT data of the subject's eye and the front image of the subject's eye in which the disc hemorrhage region detected in the detection step, wherein
the analyzing step is performed to generate at least one of the position information, the shape information, or the occurrence information, using the OCT data on which position matching has been performed with the front image in the position matching step.

25. A computer readable non-transitory recording medium in which a program for causing a computer to execute each step of the ophthalmic information processing method of claim 14 is recorded.

* * * * *